(12) United States Patent
Giese et al.

(10) Patent No.: US 11,866,779 B2
(45) Date of Patent: Jan. 9, 2024

(54) JETTISON-MS FOR NUCLEIC ACID SPECIES

(71) Applicant: Northeastern University, Boston, MA (US)

(72) Inventors: Roger W. Giese, Hanover, MA (US); Poguang Wang, Westborough, MA (US)

(73) Assignee: Northeastern University, Boston, MA (US)

( * ) Notice: Subject to any disclaimer, the term of this patent is extended or adjusted under 35 U.S.C. 154(b) by 853 days.

(21) Appl. No.: 16/961,074

(22) PCT Filed: Feb. 28, 2019

(86) PCT No.: PCT/US2019/020103
§ 371 (c)(1),
(2) Date: Jul. 9, 2020

(87) PCT Pub. No.: WO2019/169163
PCT Pub. Date: Sep. 6, 2019

(65) Prior Publication Data
US 2021/0062257 A1      Mar. 4, 2021

Related U.S. Application Data

(60) Provisional application No. 62/636,685, filed on Feb. 28, 2018.

(51) Int. Cl.
*C12Q 1/68* (2018.01)
*C12Q 1/6872* (2018.01)

(52) U.S. Cl.
CPC ..... *C12Q 1/6872* (2013.01); *C12Q 2523/313* (2013.01)

(58) Field of Classification Search
CPC .......... C12Q 1/6872; C12Q 2523/313
USPC ........... 250/281, 282, 288
See application file for complete search history.

(56) References Cited

U.S. PATENT DOCUMENTS

| | | |
|---|---|---|
| 2001/0055811 A1 | 12/2001 | Hillenkamp |
| 2003/0207460 A1 | 11/2003 | Kitagawa |
| 2009/0075295 A1* | 3/2009 | Lindsey ............... G01N 21/643 436/164 |
| 2009/0227553 A1* | 9/2009 | Lindsey ............... C07D 487/22 548/402 |
| 2009/0297456 A1* | 12/2009 | Borbas ............... A61P 35/00 424/9.61 |

(Continued)

FOREIGN PATENT DOCUMENTS

WO   WO-2019/169163 A1   9/2019

OTHER PUBLICATIONS

Gaston et al., "The identification and characterization of non-coding and coding RNAs and their modified nucleosides by mass spectrometry," RNA Biology, 11(12):1568-1585 (2015).

(Continued)

*Primary Examiner* — Nicole M Ippolito
(74) *Attorney, Agent, or Firm* — Dana M. Gordon; Foley Hoag LLP

(57) ABSTRACT

MALDI-MS operated slightly under matrix storm conditions with a high-energy-transfer, acidic matrix, or these conditions with a high sample to matrix ratio, can with ultrasensitivity detect a nucleobase, modified or canonical, of a nucleic acid species as a jettisoned, protonated molecule.

20 Claims, 22 Drawing Sheets

(56) References Cited

U.S. PATENT DOCUMENTS

2018/0024123 A1    1/2018  Giese et al.
2022/0249708 A1*  8/2022  MacNevin ............. C09K 11/06

OTHER PUBLICATIONS

International Search Report and Written Opinion for International Application No. PCT/US2019/020103 dated Apr. 30, 2019.
Nordhoff et al., "comparison of IR- and UV-matrix-assisted laser desorption/ionization mass spectrometry of oligodeoxynucleotides," Nucleic Acids Res, 22(13):2460-2465 (1994).
Wang et al., "recommendations for Quantitative Analysis of Small Molecules by Matrix-Assisted Laser Desorption Ionization Mass Spectrometry," J Chromatogr A, 1486:35-41 (2017).

* cited by examiner

JETTISON-MS FOR NUCLEIC ACID SPECIES

RELATED APPLICATIONS

This application is a § 371(c) National Stage of PCT/US2019/020103, filed Feb. 28, 2019; which claims the benefit of priority to U.S. Provisional Patent Application Ser. No. 62/636,685, filed Feb. 28, 2018.

GOVERNMENT SUPPORT

This invention was made with government support under Grant No. P42-ES017198 awarded by the National Institutes of Health. The government has certain rights in the invention.

BACKGROUND

Nucleic acid species (nucleosides, nucleotides, oligonucleotides, and nucleic acids of both DNA and RNA types) can contain canonical and as well as modified nucleobases, and the modifications can be classified as damage, natural, or synthetic. For a damaged DNA nucleic acid species, the damage commonly arises from exposure to genotoxic conditions, and the damage is commonly referred to as "DNA adduct(s)". The natural modifications of DNA fall into the field of epigenetics. For RNA, mostly natural modifications are of general interest; they play a role in the structure and function of several kinds of RNA molecules. For synthetic nucleic acid species, intended or unintended modifications arising during synthesis, termed "synthetic", also are of interest.

It has been known for about 25 years that nucleobases, canonical as well as modified, can be lost when nucleic acid species are subjected to Matrix-Assisted Laser Desorption/Ionization Mass-Spectrometry (MALDI-MS) (Stemmler E A, 1994; Stemmler E A, 1995). This is not surprising since the N-glycosidic bond in such species can be relatively labile. Through the years, this event mainly has been regarded as a nuisance, since it has limited the ability of MALDI-MS to define the masses of oligonucleotides: nucleobase loss triggers strand cleavage, progressively leading to loss of the molecular ion as strand length increases, especially above an 80 mer or so (van den Boom and Berkenkamp, 2007; Gao et al., 2013; Giessing and Kirpekar, 2012; Douthwaite, 2007; Nordhoff et al., 1996; Honisch, 2016). As the reviews indicate, nucleobase loss from glycolytic cleavage can occurs more readily from DNA than RNA, and more readily from the more basic bases A, C, and G, compared to T.

The phenomenon of nucleobase loss in MALDI MS of nucleic acid species has not evoked much interest in the detection of modified nucleobases in this way since there has been no demonstration of ultrasensitivity (e.g., detection of about 5 fmol of such species at a signal-to-noise ratio [S/N] of about 100), which is so important in working with nucleic species from biosamples. Instead researchers have turned to liquid chromatography electrospray ionization MS for modified nucleobase analysis, where many modified nucleobases of deoxynucleosides can be detected with ultrasensitivity. In this latter technique, deoxynucleosides are formed from nucleic acids by enzymatic digestion prior to injection into the instrument, and then protonated nucleobases arise for detection (Balbo, S., 2014). Unfortunately, two or more days of work are required to complete the process of digestion and analysis by liquid chromatography electrospray MS once the nucleic acid has been isolated.

Analysis of DNA Modifications.

DNA adducts are an important class of analytes, which has been reviewed (Villeta and Balbo, 2017; Balbo et al., 2014; Pottenger et al., 2014; Stornetta et al., 2016; Poirier, 2016). DNA adducts tend to be challenging to measure because of their diversity and low concentrations in biosamples. While $^{32}$P-postlabeling and immunoassays are used to measure DNA adducts, these methods have limitations in scope and accuracy (Balbo et al., 2014). DNA adductomics assays which measure multiple DNA adducts in a single procedure based on mass spectrometry are of greatest interest (Villeta and Balbo, 2017). However, the existing assays are laborious and fail to detect polar and nonpolar adducts in a single procedure (Villeta and Balbo, 2017; Taghizadeh et al., 2008; Hemeryeld et al., 2015; Wu et al., 2017; Monien et al., 2014). For example, only bulky nonpolar adducts may be detected since they elute late in the reversed-phase High Performance Liquid Chromatography (HPLC) separation where background signals have diminished. The early-eluting, polar DNA adducts are buried in the high level of noise in the early region of such a chromatogram and thereby fail to be detected under these conditions. On the other hand, different LC conditions can be used to detect small or polar adducts when relatively abundant (Taghizadeh et al., 2008; Wu et al., 2017). Another big problem with current methods for DNA adductomics is the great variation of sensitivity. For example, Monien et al. (2014) reported that limits of detection (LODs) for different DNA adducts ranged from 0.02 to 23.7 adducts in $10^8$ nucleotides, a 1000-fold range.

Analysis of RNA Modifications.

Small modifications of RNA have been reviewed in the literature (Cantara et al., 2010; Yu, et al., 2010; Satterlee, et al., 2014; Li et al., 2014; He, 2010). Several classes of RNA molecules, including tRNA, rRNA, mRNA, snoRNA, miRNA and therapeutic RNA, undergo natural or synthetic modifications to one degree or another that are critical to their structures and functions. The leading technique to assess these modifications both qualitatively and quantitatively is Liquid Chromatography-Electrospray Ionization-MS/MS tandem mass spectroscopy (LC-ESI-MS$^2$), coupled with prior enzymatic digestion to oligomers or nucleosides (Paulines, et al., 2017; Giessing, et al., 2012; Su et al., 2014; Basanta-Sanchez et al., 2015; Gatson, et al., 2014). Using these techniques, the sequence positions of the modifications sometimes can be defined. MALDI-MS also has been used to similarly study RNA modifications after enzymatic hydrolysis (Gao, et al., 2013; Douthwaite and Kirpekar, 2007).

SUMMARY

In some embodiments, the present invention relates to a mass spectrometry method for detecting a modified nucleobase in a nucleic acid species, comprising providing a sample, wherein the sample comprises: a modified nucleobase attached in N-glycosidic linkage to a ribose or deoxyribose moiety of a nucleic acid, nucleoside, nucleotide or oligonucleotide; and a matrix, wherein the matrix comprises at least one Brønsted acidic proton source. The mass spectrometry method further comprises subjecting the sample to at least one laser pulse, wherein the laser fluence is about 70% to about 95% of the matrix storm level.

In certain embodiments, the present invention relates to a mass spectrometry method for detecting a modified nucleobase in a nucleic acid species, comprising providing a sample, wherein the sample comprises: a modified nucleobase attached in N-glycosidic linkage to a ribose or deoxyribose moiety of a nucleic acid, nucleoside, nucleotide or oligonucleotide; and a matrix, wherein the matrix comprises at least one Brønsted acidic proton source and wherein the molar ratio of the overall nucleobases in the sample to the matrix is about 0.03 to about 0.3. The mass spectrometry method further comprises subjecting the sample to at least one laser pulse, wherein the laser fluence is about 70% to about 95% of the matrix storm level.

In some embodiments, the present invention relates to a mass spectrometry method for detecting a canonical nucleobase in a nucleic acid species, comprising providing a sample, wherein the sample comprises: a canonical nucleobase attached in N-glycosidic linkage to a ribose or deoxyribose moiety of a nucleic acid, nucleoside, nucleotide or oligonucleotide; and a matrix, wherein the matrix comprises at least one Brønsted acidic proton source and wherein the molar ratio of the overall nucleobases in the sample to the matrix is about 0.03 to about 0.3. The mass spectrometry method further comprises subjecting the sample to at least one laser pulse, wherein the laser fluence is about 70% to about 95% of the matrix storm level.

DETAILED DESCRIPTION

Figure 1:
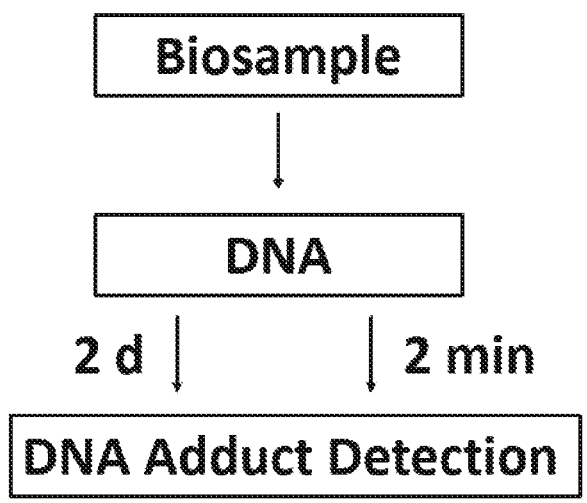
FIG. 1. Schematic depiction of two pathways for detection of DNA adducts using Mass Spectrometry: conventional (left) and Jettison-MS (JeMS, right)

The detailed description is provided to assist the reader in gaining a comprehensive understanding of the devices and methods described herein. Accordingly, various changes, modification, and equivalents of the devices and methods described herein will be suggested to those of ordinary skill in the art. The progression of fabrication operations described are merely examples, however, and the sequence type of operations is not limited to that set forth herein and may be changed as is known in the art, with the exception of operations necessarily occurring in a certain order. Also, description of well-known functions and constructions may be omitted for increased clarity and conciseness.

MALDI-TOF MS (matrix-assisted laser desorption ionization time of flight mass spectrometry) involves laser pulses focused on a small sample spot on a sample plate comprising analyte molecules (e.g., oligonucleotides) embedded in either a solid or liquid matrix comprising a small, highly laser-energy absorbing compound. The laser pulses transfer energy to the matrix causing a microscopic ablation and concomitant ionization of the analyte molecules, producing a gaseous plume of intact and/or fragmented charged analytes. The ions generated by the laser pulses are accelerated to a fixed kinetic energy by a strong electric field and then pass through an electric field-free region in vacuum in which the ions travel with a velocity corresponding to their respective mass-to-charge ratios (m/z). The smaller m/z ions will travel through the vacuum region faster than the larger m/z ions thereby causing a separation. At the end of the electric field-free region, the ions collide with a detector that generates a signal as each set of ions of a particular mass-to-charge ratio strikes the detector. Usually for a given assay, 100 to 400 mass spectra resulting from individual laser pulses are summed together to make a single composite mass spectrum with an improved signal-to-noise ratio.

The mass of an ion (such as a charged oligonucleotide) is measured by using its velocity to determine the mass-to-charge ratio by time-of-flight analysis. In other words, the mass of the molecule directly correlates with the time it takes to travel from the sample plate to the detector. The entire process takes only microseconds. In an automated apparatus, multiple samples can be analysed per minute. In addition to speed, MALDI-TOF MS has one of the largest mass ranges for mass spectrometric devices.

As used herein "nucleic acid species" refers to nucleosides, nucleotides, oligonucleotides, and nucleic acids of either RNA type or DNA type, and also synthetic analogs such as those having phosphorothiolate diester linkages, which have canonical nucleobases comprising adenine, guanine, cytosine, and thymine (for DNA-type nucleic acid species), or uracil instead of thymine (for RNA-type nucleic acid species), and sometimes modified nucleobases.

As used herein, "canonical nucleobase" refers to one of the five nucleobases contained in DNA and RNA: adenine (A), cytosine (C), guanine (G), thymine (T), and uracil (U).

As used herein, "mass spectrometry" encompasses any suitable mass spectrometric format known to those of skill in the art. Such formats include, but are not limited to, Matrix-Assisted Laser Desorption/Ionization, Time-of-Flight (MALDI-TOF), Electrospray Ionization (ESI), IR (infrared)-MALDI (see, e.g., published International PCT application No. 99/57318 and U.S. Pat. No. 5,118,937), Orthogonal-TOF (O-TOF), Axial-TOF (A-TOF), Linear/Reflectron (RETOF), Ion Cyclotron Resonance (ICR), Fourier Transform and combinations thereof.

As used herein, "matrix" is a material used in MALDI mass spectrometry, which customarily is present in large excess relative to the analyte, serving to absorb energy from the laser pulse and to transform it into thermal and excitation energy to desorb and ionize the analyte. In certain embodiments, a matrix is selected from the group consisting of sinapinic acid, α-cyano-4-hydroxycinnamic acid, 4-chloro-α-cyanocinnamic acid 2,5-dihydroxybenzoic acid, 3-hydroxypicolinic acid, 5-(trifluoro-methyl)uracil, caffeic acid, succinic acid, anthralinic acid, 3-aminopyrazine-2-carboxylic acid, ferulic acid, 7-amino-4-methyl-coumarin, 2,4,6-trihydroxyacetophenone, and 2-(4-hydroxyphenylazo)-benzoic acid. In UV MALDI, high-energy-transfer matrices are also referred to as "high energy or hot", as opposed to "low energy or cold".

Examples of high energy matrices are alpha-cyano-4-hydroxycinnamic acid [CCA], 4-chloro-alpha-cyanocinnamic acid [ClCCA], indole acetic acid [IAA] and 2-mercaptobenzothiazole [MBT].

For IR-MALDI, matrices such a, glycerol, succinic acid, urea, and 3-hydroxypicolinic acid have been used to test oligonucleotides. Reagents for UV MALDI can also work well in IR MALDI (Zenobi, R., 1998).

As used herein, the "matrix storm level" refers to the minimum laser fluence level that launches excessive matrix signals, swamping out analyte signals, and rendering the MALDI experiment meaningless. At this level, one may observe a significant depletion (where the visualization is done with a camera or monitor) of a solid MALDI spot. As used herein, the phrase "mass spectrometric analysis" refers to the determination of the charge to mass ratio of ionized atoms, molecules or molecule fragments.

As used herein, mass spectrum refers to the presentation of data obtained from analyzing a biopolymer or fragment thereof by mass spectrometry either graphically or encoded numerically or otherwise presented.

As used herein, pattern with reference to a mass spectrum or mass spectrometric analyses, refers to a characteristic distribution and number of signals, peaks or digital representations thereof.

As used herein, signal, peak, or measurement, in the context of a mass spectrum and analysis thereof refers to the output data, which can reflect the charge to mass ratio of an ionized atom, molecule or fragment of a molecule, and also can reflect the amount of the ionized atom, molecule, or fragment thereof, present. The charge to mass ratio can be used to determine the mass of the atom, molecule or fragment of a molecule, and the amount can be used in quantitative or semi-quantitative methods. For example, in some embodiments, a signal peak or measurement can reflect the number or relative number of molecules having a particular charge to mass ratio. Signals or peaks include visual, graphic and digital representations of output data.

As used herein, intensity, when referring to a measured mass, refers to a reflection of the relative amount of an analyte present in the sample or composition compared to other sample or composition components. For example, an intensity of a first mass spectrometric peak or signal can be reported relative to a second peak of a mass spectrum, or can be reported relative to the sum of all intensities of peaks. One skilled in the art can recognize a variety of manners of reporting the relative intensity of a peak. Intensity can be represented as the peak height, area under the peak, signal to noise (S/N) ratio, or other representations known in the art.

As used herein, comparing measured masses or mass peaks refers to analyzing one or more measured sample mass peaks relative to one or more sample or reference mass peaks. For example, measured sample mass peaks can be analyzed by comparison with a calculated mass peak pattern, and equivalence between measured mass peaks and calculated mass peaks can be determined to help identify the sample mass or molecule. A reference mass peak is a representation of the mass of a reference ionized atom, molecule or fragment of a molecule.

As used herein, a reference mass is a mass with which a measured sample mass can be compared. A comparison of a sample mass with a reference mass can help to identify a sample mass as the same as or different from the reference mass. Such a reference mass can be calculated, can be present in a database or can be experimentally determined. A calculated reference mass can be based on the predicted mass of a nucleic acid. For example, calculated reference masses can be based on a predicted fragmentation pattern of a target nucleic acid molecule of known or predicted sequence.

As used herein, "solid support" refers to an insoluble support that can provide a surface on which or over which a reaction can be conducted and/or a reaction product can be retained at identifiable loci for MALDI purposes. Exemplary solid supports include, but are not limited to flat supports such metal-coated glass surfaces and a metal surface such steel or gold. The solid support is in any desired form suitable for mounting on a cartridge base for MALDI, including, but not limited to: a plate, membrane, wafer, a wafer with pits, a porous three-dimensional support, and other geometries and forms known to those of skill in the art. Exemplary supports are flat surfaces designed to receive samples at discrete loci, such as flat surfaces with hydrophobic regions surrounding hydrophilic loci, with the latter part for receiving a sample.

As used herein, TOF/TOF refers to a tandem mass spectrometry method where two stages of time-of-flight are used consecutively in a mass spectrometer. Two stages of mass spectrometry can also be done in an ion trap or by a stage of quadrupole mass spectrometry followed by TOF or followed by an ion trap, for example.

As used herein, a subject includes, but is not limited to, animals, plants, bacteria, viruses, parasites and any other organism or entity that has nucleic acid. Among subjects are mammals, preferably, although not necessarily, humans. A patient refers to a subject afflicted or potentially afflicted with a disease or disorder.

As used herein, "sample" refers to a nucleic species from a given material, or a given material containing a nucleic acid species. The material may be biological or synthetic. In one embodiment, the material is biological. The term "biological" refers to any material obtained from a living source, for example, an animal such as a human or other mammal, a plant, a bacterium, a fungus, a protist, or a virus. The biological material can be in any form, including a solid material such as a tissue, cells, a cell pellet, a cell extract, or a biopsy, or a biological fluid such as urine, blood, plasma, serum, saliva, sputum, amniotic fluid, exudate from a region of infection or inflammation, or a mouth wash containing buccal cells, cerebral spinal fluid, synovial fluid, organs, semen, ocular fluid, mucus, secreted fluids such as gastric fluids or breast milk, and pathological samples such as a formalin-fixed sample embedded in paraffin. In particular, herein, the sample can be mixed with matrix when mass spectrometric analyses of nucleic acid species are performed. Derived from means that the sample can be processed, such as by purification or isolation, prior to being subjected to JeMS.

As used herein, "Jettison-MS" is abbreviated JeMS, and includes the tandem option abbreviated JeMS2, such as that utilizing TOF/TOF.

Jettison-MS Method

The present disclosure relates to a method for the detection of modified nucleobases of small nucleic acid species, namely of nucleosides, nucleotides and oligonucleotides of either the DNA or RNA type, or related synthetic types such as those having one or more phosphorothiolate diester linkages. The disclosed method also allows for the detection of modified nucleobases in nucleic acid species which are nucleic acid of either the DNA or RNA type or mixed. In both cases, the nucleic acid species is directly subjected to MALDI-MS, such as a MALDI-TOF-MS or a MALDI-TOF/TOF-MS (rather than undergoing enzymatic hydrolysis, extraction, and HPLC prior to MS into order to detect modified nucleobases).

The present disclosure relates to a MALDI-MS method, referred to as "Jettison-MS", which can provide ultrasensitive detection of modified as well as canonical nucleobases in nucleic acid species in a rapid and simple way. This is achieved by using a combination of three conditions in the MALDI experiment for nucleosides, nucleotides, and oligonucleotides: acidity, high-energy-transfer matrix, and laser fluence just below the matrix storm level. For nucleic acids, an additional condition is used: the molar ratio of the overall nucleobase content of the sample to the matrix compound is in the range of 0.03 to 0.3 (unusually high). The acidity can be established by employing a matrix compound containing a carboxylic acid moiety, or by including an acid such as ammonium chloride, phosphoric acid, acetic acid, formic acid, trifluoroacetic acid, or heptafluorobutyric acid. For UV MALDI, high-energy-transfer matrices are also referred to as "high energy or hot", as opposed to "low energy or cold". The "matrix storm level" refers to the minimum laser fluence level that launches excessive matrix signals, swamping out analyte signals, and rendering the MALDI experiment meaningless. At this level, one also may observe a significant depletion (where the visualization is done with a camera or monitor) of a solid MALDI spot. In Jettison-MS, a laser fluence is employed which is in the range of about 0.7 to 0.95 of the matrix storm level, and preferably about 0.90 to 0.95. The main advantage of Jettison-MS is that data (signal from jettisoned, protonated nucleobases of interest) is acquired within minutes once the nucleic acid species is isolated in a purified form, as opposed to days with methodology based on enzymatic digestion liquid chromatograph electrospray ionization mass spectrometry. The enzymatic digestion can also be expensive.

The disclosed procedure, Jettison MS, has the following advantages: (1) it eliminates 2-3 days of sample preparation (FIG. 1); (2) a diversity of modifications (both polar and nonpolar) can be detected in a single procedure (adductomics); and (3) the technique allows for high throughput testing (e.g., 20 spotted DNA samples have been tested by JeMS in 30 minutes). As shown herein, this method is useful for such applications as detection of hydroxymethylcytosine in human brain DNA and detection of melphalan DNA adducts in patients given melphalan to treat multiple myeloma.

Figure 2:
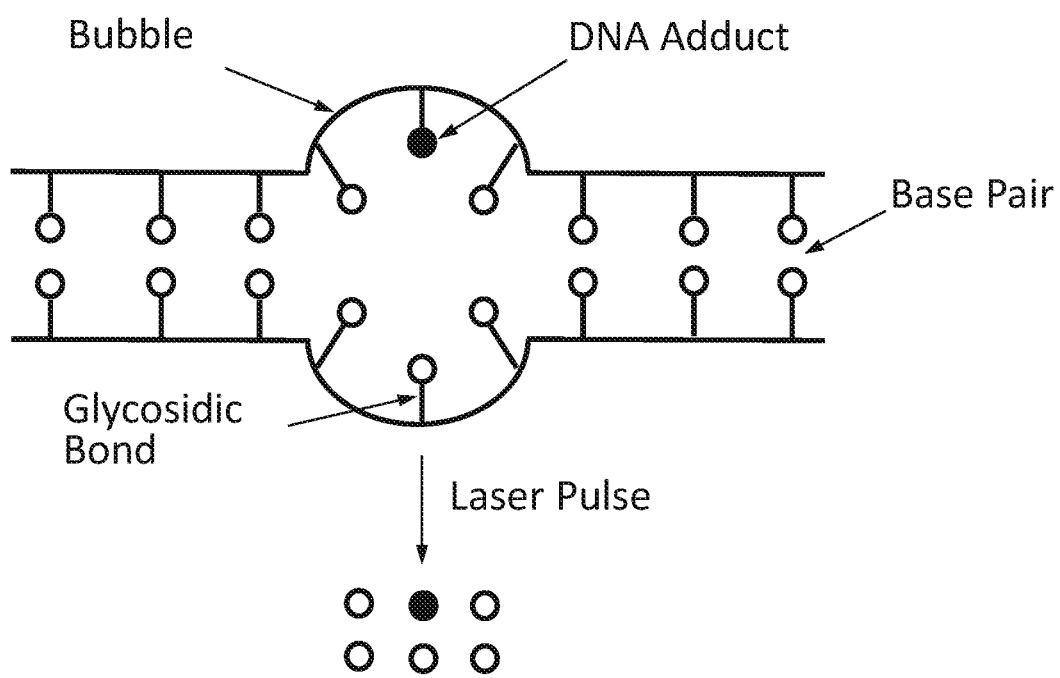
FIG. 2. Bubble strategy for the Jettison-MS ("JeMS", which may be Jettison MS in an MS/MS mode, termed "JeMS2") analysis of DNA adducts in double stranded DNA, where the DNA adduct causes a disruption referred to as a "bubble".

For DNA samples, the modifications of interest are DNA adducts, which are detrimental to DNA, and thereby the cell, because of their potential to be converted into mutations. Many DNA adducts make a "bubble" of one sort or another on DNA, in which there is loss of base-pairing of the nucleobases in this region (Geacintov and Broyde, 2010). Such adducts are likely more than to be released under MALDI conditions, giving satellite peaks, relative to non-bubble-forming DNA (FIG. 2). Certain DNA adducts, which actually strengthen the DNA molecule, might be preferentially detected by their enhanced ability to recruit matrix molecules and/or loosen DNA in the presence of a matrix. Also of interest are natural or sometimes natural modifications such as 5-methylcytosine, 5-hydroxymethylcytosine, 5-formylcytosine, and 5-carboxycytosine.

Small modifications of nucleic acids, both DNA and RNA, can be measured using the Jettison-MS method in a convenient, omics way. Current methods for measuring such modifications have shortcomings that our method can overcome. For example, a recent attempt to measure 8-oxo-G DNA adducts in skin samples using a commercial immunoassay kit for this purpose, encountered intense and variable background signals. While there are LC-MS assays for this adduct, they are tedious (Talhizadeh et al., 2008; Wu et al., 2017).

Intercalators. Intercalators can be employed in Jettison-MS, such as caffeine, cholesterol and thalidomide. Intercalators tend to perturb and destabilize DNA structure, as has been reviewed in the literature (Hendry et al., 2007), and thereby may reduce canonical nucleobase signals. The effect of an intercalator in a MALDI matrix may differ from its effect in a buffer.

Matrix-Free Laser Desorption. The invention of MALDI-MS was very important and led to a Nobel Prize. For Jettison-MS, a special case, it is conceivable that a typical matrix is not required. Studies may be performed using known matrix-free laser desorption conditions, a subject that has been reviewed (Rainer et al., 2011; Peterson, 2007).

Spotting. A standard MALDI plate allows for introduction of 0.7 µL of sample/matrix solution, forming a 2 mm dried spot. For example, a dried nucleic acid species can be dissolved in 4 µL of water and mixed with 2 µL of matrix solution (such as 5 mg/mL of CCA in 50% acetonitrile). Anchor plates with 0.7 mm polar spots surrounded by a hydrophobic layer (Hudson Surface Technology Company) allow for larger sample volumes to be introduced. By employing a more dilute matrix, 2 µL of the 6 µL sample with much lower amount of matrix can be introduced in triplicate onto the Hudson plate. This procedure allows for reducing of the sample amount to 60 ng from the typical 500 ng of DNA, thereby making the method more applicable to small biological samples.

Jettison-MS with CCA-Substituted Probes. Ordinarily the matrix, e.g., α-cyano-4-hydroxycinnamic acid (CCA), is used as a bulk material in MALDI. Since nucleic acids exhibit negligible absorption at the wavelength of the MALDI laser, the technique can focus the laser energy onto bubbled regions of DNA by enriching the matrix at those sites via CCA-coupled probes. The method can subject DNA to MALDI-TOF/TOF-MS with little or no matrix but in the presence of a random mixture of tri- or tetra-nucleotides, where each nucleotide oligomer has an alkylamine leash to which a molecule of matrix is attached. The experiment is conducted as follows. A totally randomized 3-mer having a 3'-aminohexyl modifier is prepared by subjecting the 3'-amino-modifier C7 CPG 1000 (Glen Research) to three rounds of coupling with equimolar mixture of the four canonical phosphoramidites (Glen Research). The product is obtained by synthesis at the 1.0 µmol level. 4-Chloro-α-cyanocinnamic acid as an NHS ester is coupled to the 3'-aminohexyl chain of random 3-mers and, separately, to random 4-mers. An n-mer mixture at the 1.0 µmol level is 3000× on a molar basis more material than 100 ng of DNA, which is enough for several experiments.

Jettison-MS with a dedicated pulsed laser to excite the N-glycosidic bond. The targeted N-glycoside bond cleavage could be enhanced with two synchronized laser pulses: the first laser pulse will stimulate the targeted N-glycoside bond (unpaired nucleobase in the nucleic acid bubble) by vibronic or vibrational excitation; the second pulsed laser, the original MALDI laser, synchronized or delayed by a short vibrational period (~ps) will pump the matrix as well as cleaved nucleobase ions into the gas phase. The wavelength and pulse duration of the first laser should be optimized for targeted N-glycoside bond cleavage.

Alternative Matrix JeMS. Many matrices are available for MALDI. We have reviewed this subject (Wang and Giese, 2017) including citing several other reviews. So far four matrices have been tested in Jettison-MS: alpha-Cyano-4-hydroxycinnamic acid (CCA), 4-chloro-α-cyanocinnamic acid (chloro-CCA), 2,5-Dihydroxybenzoic acid (DHB), and trihydroxyacetophenone (THAP). The tested matrices provided satisfactory data in the Jettison-MS experiments, but sensitivity was 10-fold lower with DHB or THAP (low energy matrix). Choro-CCA gave the same sensitivity overall as CCA. Other matrices may overcome matrix interference peaks, and different matrices may solvate modified bases differently. Other matrices, especially those that have been previously used for nucleic acids (Wu et al., 1993) can be tested for their performance in Jettison-MS experiments.

Sometimes JeMS2 will yield a peak for the canonical nucleobase, when the adducted chemical falls off. For example, N6-isopentenyladenine was detected in RNA this way by observing an ion for protonated adenine in JeMS2. Another approach is to compare data from two sets of samples, e.g., samples collected from obese and non-obese subjects.

Potential Contribution of this Research to Scientific Field(s) and Public Health.

(1) Regulatory Decisions. It is well established that there are chemical-induced cancers, making it important to have DNA adduct data in making regulatory decisions (Poirier, 2016).

(2) Cancer Prevention. This project can yield a test that may help to prevent some cancer. In this test, DNA from a sample of a person's blood can be screened for DNA adducts by Jettison-MS. Some individuals, because of their unique combination of exposures (in the broadest sense, including diet and lifestyle) along with variation in metabolism including DNA repair, may have an elevated level of some DNA adducts that increases their risk for cancer. If an individual had this information, she or he may be able to modify their exposure in a personalized way to lower cancer risk.

(3) Sentinel Monitoring. The use of selected animals and plants as "sentinel species" which serve as harbingers of dangers to human health and environment has been reviewed in the literature (Ritter 2017). Monitoring DNA adducts in these species can extend the usefulness of sentential monitoring.

(4) Obesity. Obesity is a cause of cancer (Hursting et al., 2015), possibly through the formation of DNA adducts. Monitoring of DNA adducts in obese individuals might allow for early detection and prevention of cancer.

(5) DNA repair targeted therapies. There is a need for biomarkers of response and resistance in DNA repair targeted therapies (Stover et. al., 2016). The Jettison-MS assay can be helpful for this purpose.

(6) Nervous System. Modifications of RNA molecules play a role in the activity of some of the RNA molecules in the nervous system (Satterlee et al., 2014) and there is a need to monitor these modifications more efficiently.

Attractive Features of Jettison-MS Detection of Nucleic Acid Modifications:

High speed, and low cost: no enzyme digestion and LC separation involved, usually a few minutes per sample.

Broad range detection (covers polar and non-polar modified bases) with structure information by MS/MS.

Capable to detect metastable DNA adducts.

Low sample consumption.

DNA could be purified easily by isopropanol precipitation/cold ethanol wash or membrane filtration, and CCA matrix by recrystallization (for example, form an acetonitrile solution). Intact DNA does not interfere with the low mass adduct detection above the known CCA background. FTMS or ion mobility MS could help too.

Easier detection of small modifications of nucleic acids in an adductome mode.

Advantages of Jettison-MS Detection of Nucleic Acid Modifications Over Other Existing Methods:

LC/MS methods are time consuming, difficult to achieve detection of polar and non-polar adducts in a single run, and can introduce artefacts from the long/multistep process.

Antibody-based methods are limited by the availability of the specific antibody; only one analyte is detected per test; problems with specificity and background signals are common.

Ames assay lacks chemical details for the drug candidate being screened, and it is a bacteria-based assay. This slow, expensive, vague assay is widely in drug development because it is the best tool available.

In comparison, Jettison-MS is a high throughput, low cost method, capable of processing hundreds of samples of nucleic acid species in hours. It is a broad range method that can reveal the chemical nature of nucleobase modification in an intact nucleic acid. It would be a great follow-up test to the Ames assay, and the FDA encourages a specific test for DNA adducts in a specific way, but no technology has been realistic for this challenge until the present disclosure.

Potential Commercial Applications of Jettison-MS Method:
Drug screening
Clinical diagnostic test for cancer detection and prevention
Test for animal sentinel monitoring
Repairome test
Testing at an analytical testing lab
Chemotherapy drug monitoring
Oxidative DNA damage test
DNA adductome test Jettison-MS is a technique ready to be used for nucleic acid species (e.g., DNA or RNA) testing, chemotherapy monitoring, animal and cell culture exposure testing, drug screening, repairome testing.

In some embodiments, the present invention relates to a mass spectrometry method for detecting a modified nucleobase in a nucleic acid species, comprising providing a sample, wherein the sample comprises: a modified nucleobase attached in N-glycosidic linkage to a ribose or deoxyribose moiety of a nucleic acid, nucleoside, nucleotide or oligonucleotide; and a matrix, wherein the matrix comprises at least one Brønsted acidic proton source. The mass spectrometry method further comprises subjecting the sample to at least one laser pulse, wherein the laser fluence is about 70% to about 95% of the matrix storm level.

In certain embodiments, the present invention relates to a mass spectrometry method for detecting a modified nucleobase in a nucleic acid species, comprising providing a sample, wherein the sample comprises: a modified nucleobase attached in N-glycosidic linkage to a ribose or deoxyribose moiety of a nucleic acid, nucleoside, nucleotide or oligonucleotide; and a matrix, wherein the matrix comprises at least one Brønsted acidic proton source and wherein the molar ratio of the overall nucleobases in the sample to the matrix is about 0.03 to about 0.3. The mass spectrometry method further comprises subjecting the sample to at least one laser pulse, wherein the laser fluence is about 70% to about 95% of the matrix storm level.

In some embodiments, the present invention relates to a mass spectrometry method for detecting a canonical nucleobase in a nucleic acid species, comprising providing a sample, wherein the sample comprises: a canonical nucleobase attached in N-glycosidic linkage to a ribose or deoxyribose moiety of a nucleic acid, nucleoside, nucleotide or oligonucleotide; and a matrix, wherein the matrix comprises at least one Brønsted acidic proton source and wherein the molar ratio of the overall nucleobases in the sample to the matrix is about 0.03 to about 0.3. The mass spectrometry method further comprises subjecting the sample to at least one laser pulse, wherein the laser fluence is about 70% to about 95% of the matrix storm level.

In certain embodiments, the laser is a UV laser.
In certain embodiments, the laser is an IR laser.
In certain embodiments, the laser fluence is about 80% to about 95% of the matrix storm level.
In certain embodiments, the laser fluence is about 90% to about 95% of the matrix storm level.
In certain embodiments, at least two synchronized laser pulses are used that differ in wavelength.

In certain embodiments, the matrix comprises glycerol, urea, or succinic acid.
In certain embodiments, the matrix comprises a compound having a carboxylic acid moiety.
In certain embodiments, the matrix comprises a compound, wherein the compound is α-cyano-4-hydroxycinnamic acid or 4-chloro-α-cyanocinnamic acid.
In certain embodiments, the Brønsted acidic proton source is selected from the group consisting of phosphoric acid, ammonium chloride, formic acid, acetic acid, trifluoroacetic acid, and heptafluorobutyric acid.

EXAMPLES

The present invention relates to a method for direct testing of a nucleic acid extracted from a biologic sample by MALDI-mass spectrometry. It needs less than 1 μg of a nucleic acid, and uses the pulsed UV laser to cleave the DNA adducts from the mismatched DNA segment or modified bases from a RNA loop region, leading to detection by MS and/or MS/MS. The analysis time is in minutes (20 spotted DNA samples have been tested in 30 minutes) compared to days needed for LC/MS methods. While already useful, the method is ready for extension in scope and sensitivity via use of enzymes or other techniques to first release one or more modified DNA or RNA segments of interest for analysis by JeMS.

Materials

Triethylamine, α-cyano-4-hydroxycinnamic acid (CCA), 4-chloro-alpha-cyanocinnamic acid (ClCCA), benzyl bromide, cyclophosphamide, Lomustine, methanesulfonic acid ethyl ester, melphalan, styrene oxide, benzyl bromide, calf thymus DNA, tRNA (Type X from baker's yeast, R9001), RNA (557111), Calf thymus DNA (CT DNA), 2-(N-morpholino)ethanesulfonic acid (MES), and *E. coli* DNA were from Sigma (St. Louis, MO). Microcentrifuge tubes, pipette tips, and HPLC grade acetonitrile (ACN) were from Fisher Scientific (Pittsburgh, PA). All materials were used as received.

Instrumentation

MALDI-TOF/TOF-MS: model 5800 from AB-SCIEX (Framingham, MA) with a frequency-tripled Nd:YAG laser at 349 nm, operated in the positive ion mode.

Benzyl-dGMP dGMP was treated with benzyl bromide under low yield conditions (dGMP at 1 mg/mL, molar ratio of 1 for BzBr to dGMP, no added base), analysed by HPLC-UV to determine the yield (5% yield, where four benzyl-G isomers were observed), and further subjected to serial dilutions and tested by Jettison-MS (JeMS). The DNA sample was diluted with water prior to testing it by JeMS.

Adducted DNA

Taking advantage of prior literature on the formation of DNA adducts from Lomustine (Moschel, 1979), methanesulfonic acid ethyl ester (Sattsangi, 1977), and styrene oxide (Schrader, 1997), DNA samples (0.5 mg/mL in 20 mM MES buffer at pH 7 with 25% ACN) were reacted at 2 mg/mL with each of those reagents, standing in the dark, at 45° C. The reaction time was overnight for Lomustine and 2 h for others. Benzylated DNA was prepared under the similar conditions for 2 h with use of 2 μL/mL triethylamine instead of MES. Each of the reaction mixtures was cooled to 0° C., and then mixed with 1/10 volume of 5 M NaCl and 0.7 volume of isopropanol, and the precipitated DNA was washed 4× with 1 mL of ice-cold 70% ethanol. Each modified DNA was re-dissolved in water at 1 mg/mL prior to testing by JeMS.

Purification of DNA from Biosamples

DNA was purified from samples of human blood buffy coat and brain using a QIAGEN Genomic Tip Kit. The DNA then was desalted by precipitation in cold, 70% aqueous ethanol and washed in this solvent. When this procedure gave inadequate removal of salt, especially with low amount of DNA, the DNA was purified further by redissolving in water and spinning in an Amicon Ultra 0.5 mL Centrifuge Filter (regenerated cellulose 3000 NMWL); discard the filtrate, add 320 μL of water:acetonitrile, 9:1, v/v: spin and discard; repeat four more times; rinse the inner surface of the filter with 50 μL of water; reverse the filter and centrifuge again to obtain 100 μL of water containing desalted DNA.

MALDI-TOF-MS and MALDI-TOF/TOF-MS: Nucleosides, Nucleotides, and Oligonucleotides One μL of an aqueous solution of a nucleoside, nucleotide(s), or oligonucleotide was added to 9 μL of CCA matrix solution (5 mg/mL in 50% ACN), and 0.7 μL was deposited as a single spot on the MALDI plate followed by drying in air. Each sample well was surveyed with the laser beam in the MS mode to find a "sweet spot" (location on a sample spot where the signal is higher), and then 400 laser pulses were averaged to generate a spectrum. The delay time was 100 ns. MS/MS spectra were obtained with a mass resolution window of 400, collision-induced dissociation gas off and the metastable-ion suppressor on.

MALDI-TOF-MS and MALDI-TOF/TOF-MS: Nucleic Acids

Two μL of a ≤1 mg/mL aqueous solution of DNA was combined with 1 μL of 5 mg/mL solution of CCA or ClCCA in acetonitrile:water, 1:1, v/v, and 0.7 μL of the resulting solution was spotted onto the MALDI target followed by 5 minutes of drying in air. The laser fluence was set at 0.8 to 0.95 of the matrix storm level. Relative calibration of signals for modified nucleobases was based on the observed intensity of adenine (136 Da) and guanine (152 Da) signals.

While abundant modifications (as in tRNA) can be detected in the TOF mode, the TOF/TOF mode usually is necessary for detection of DNA adducts. In the latter case, one either selects postulated precursor ions for TOF/TOF (targeted mode), or selects non-matrix ions in the TOF mode with a relatively low abundance (e.g., <5%) for TOF/TOF analysis (non-targeted mode).

Figure 3:
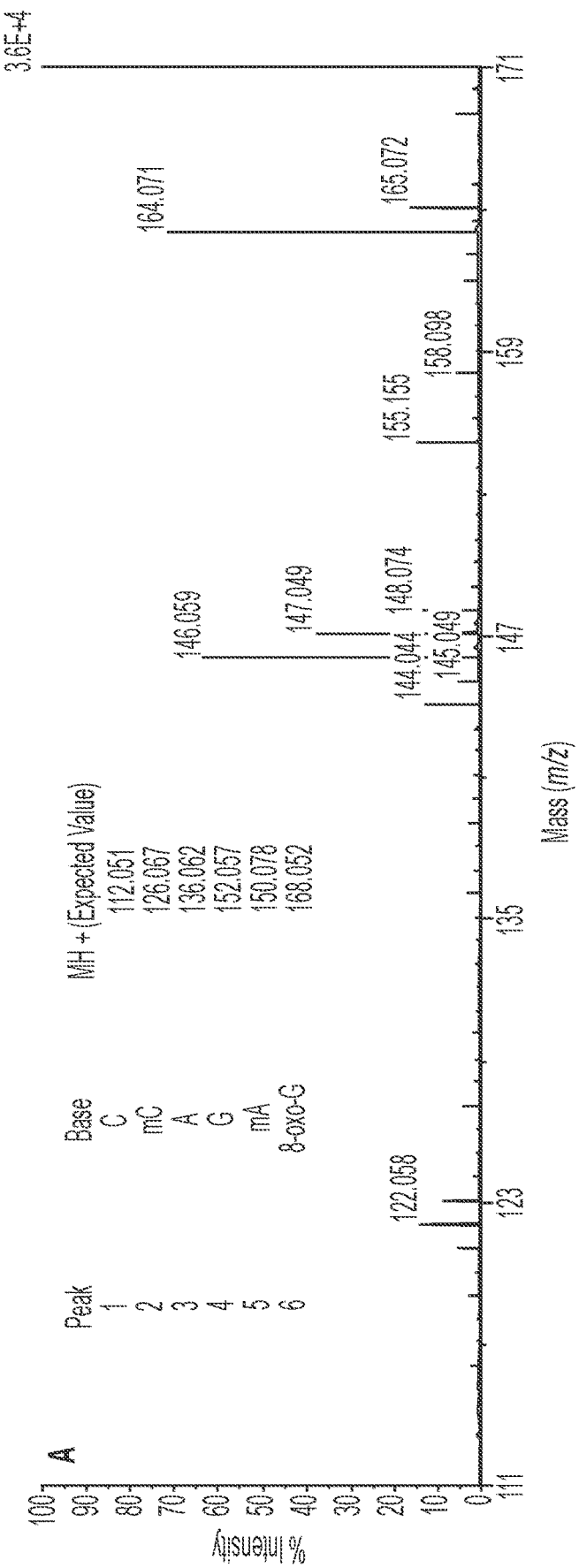
FIG. 3A. JeMS background spectrum from CCA matrix.
FIG. 3B. JeMS spectrum of calf thymus DNA: nucleobase peaks C (m/z 112), mC (m/z 126), A (m/z 136), G (m/z 152), and, possibly, 8-oxo-G (m/z 168.049). Inset I shows mA at m/z 150.079 from E. coli DNA. Inset II shows calf thymus DNA that has been treated with $H_2O_2$, displaying the enhanced peak at m/z 168.054.
Figure 3:
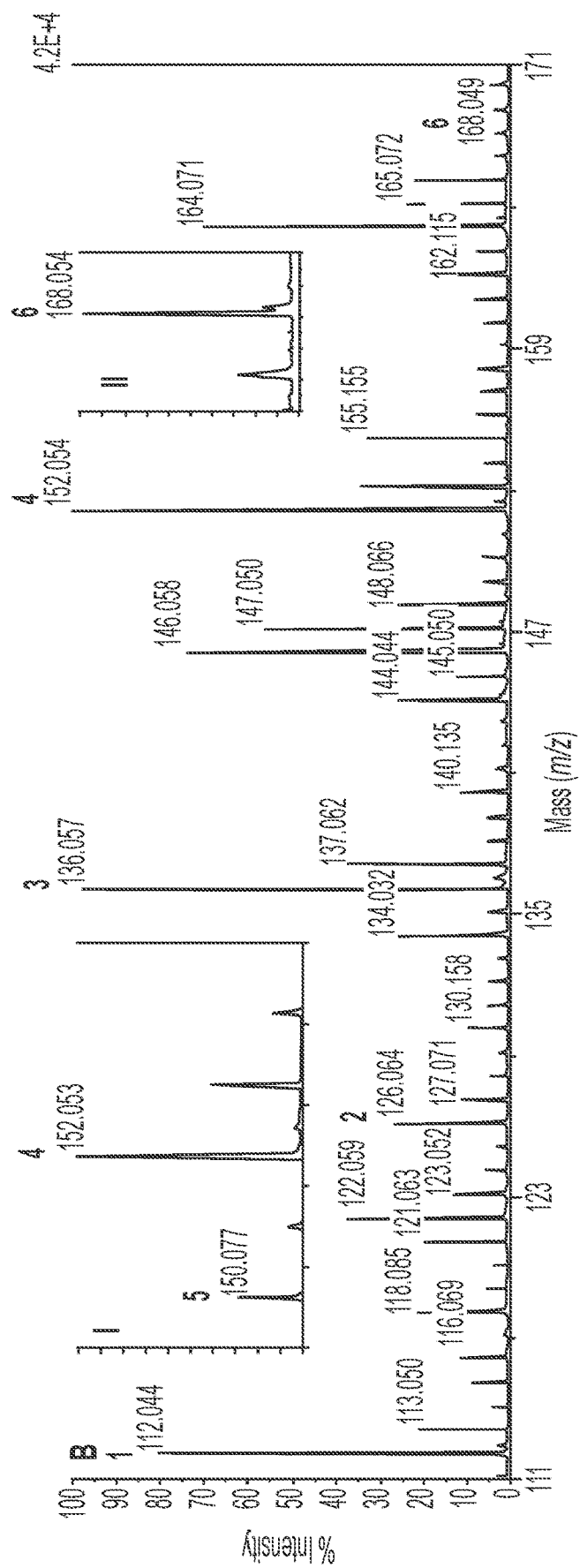

The background spectrum of the CCA matrix is shown in FIG. 3A. The analysis of calf thymus DNA by Jettison-MS in the TOF mode is shown in FIG. 3B. Consistent with prior literature as described above, peaks are seen for A, C and G but not T. The peak for 5-methylcytosine (mC) is unexpectedly high relative to C. It is possible that less polar mC engages more with CCA matrix. Additionally, saturation of the signal for C may play a role. Inset I shows a peak for N6-methyladenine at 150.077 when E. coli DNA is tested. Detection of 8-oxo-G in calf thymus DNA at m/z 168.049 is quite uncertain because of background noise, but testing the sample after treatment with hydrogen peroxide gives a peak for this compound, as seen in inset II, at m/z 168.054. Pinak (2003) calculated that 8-oxo-G is flipped out of dsDNA by electrostatic repulsion.

Figure 4:
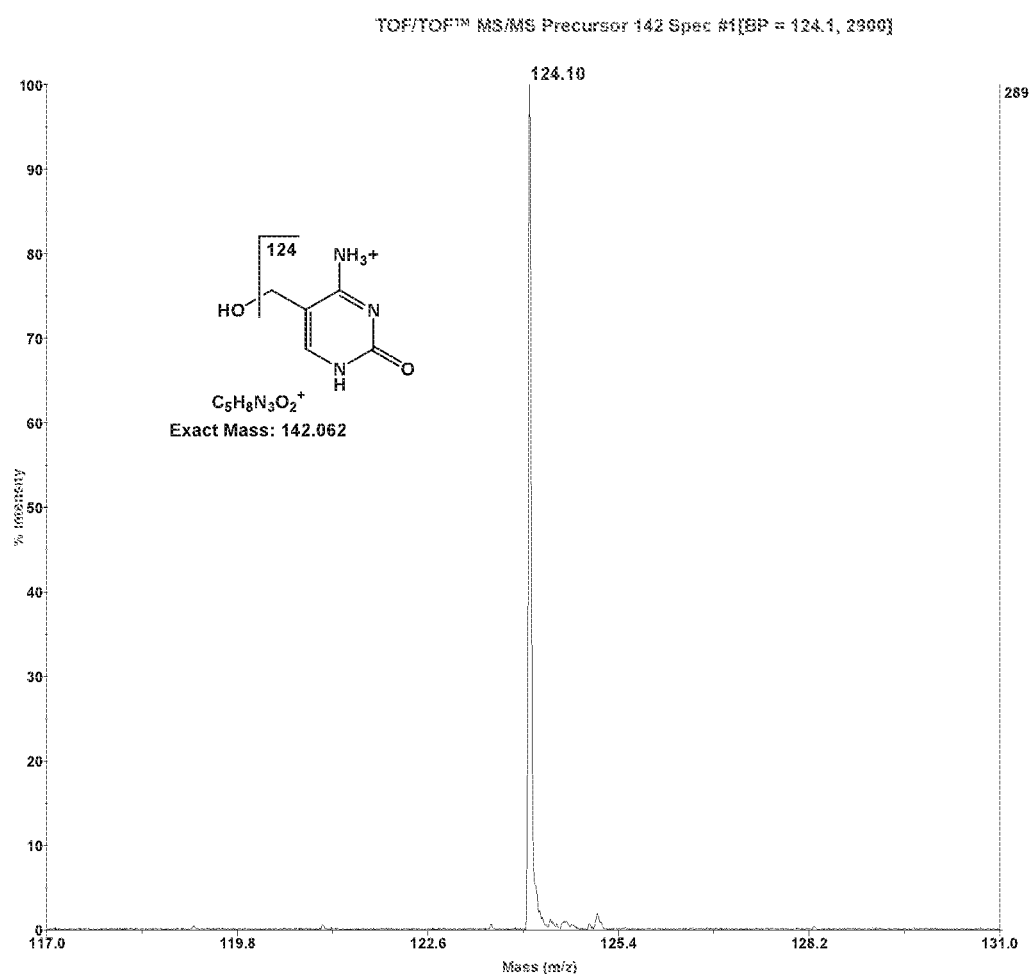
FIG. 4. JeMS2 (142→124) detects hmC from human brain DNA. The precursor ion for TOF/TOF is that of protonated hmC, which loses water to give the ion observed.

FIG. 4 demonstrates detection of 5-hydroxymethylcytosine (hmC) in human brain DNA by Jettison-MS2. The precursor ion for TOF/TOF is that of protonated hmC, which loses water to give the observed ion. DNA samples from 20 brains were tested. A correlation with aging was found by normalizing peak height for mC relative to the sum of the peaks for A+G in the TOF mode. The time on the instrument to test the 20 brain DNA samples was only 30 minutes.

Figure 5:
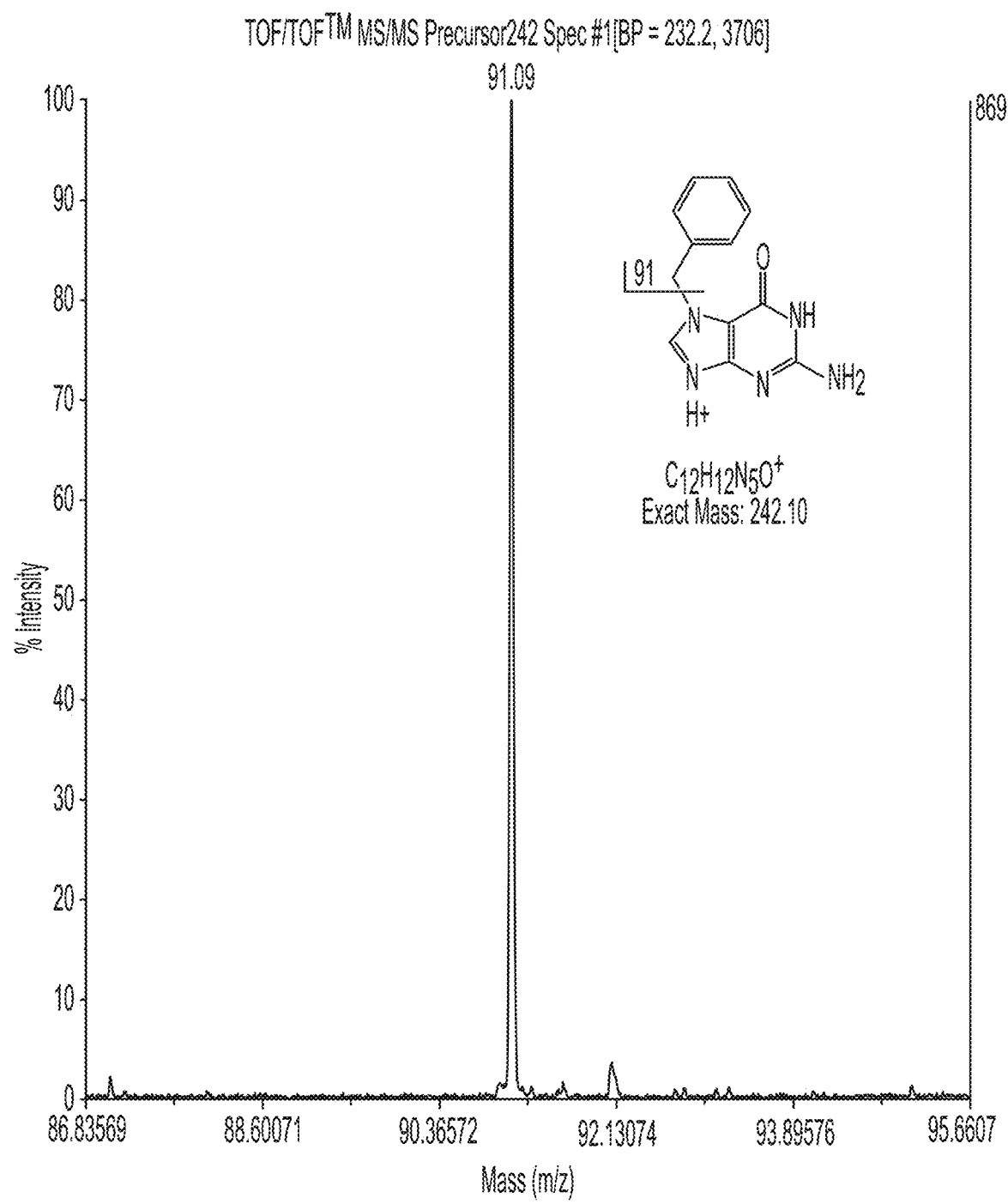
FIG. 5. JeMS2 (242→91) of Bz-G from a BzBr treated DNA.

FIG. 5 shows the detection of the benzyl ion derived as a product ion from the precursor ion of benzyl-G by Jettison-MS2, where the base is readily lost as a neutral species. The DNA had been modified with benzyl bromide. Apparently the N7-G adduct of benzyl bromide is the detected species. The positive charge in the ion makes the glycosidic bond labile, which may result in the adduct contributing to the DNA bubble formation. Many genotoxic chemicals are alkylating agents, and tend to attach to the N7 position of the purine nucleobases. However, benzyl is possibly a particularly beneficial alkyl substituent for JeMS2 because of the stability of the benzyl cation. Benzyl-A species can also be detected in a similar manner.

Figure 10:
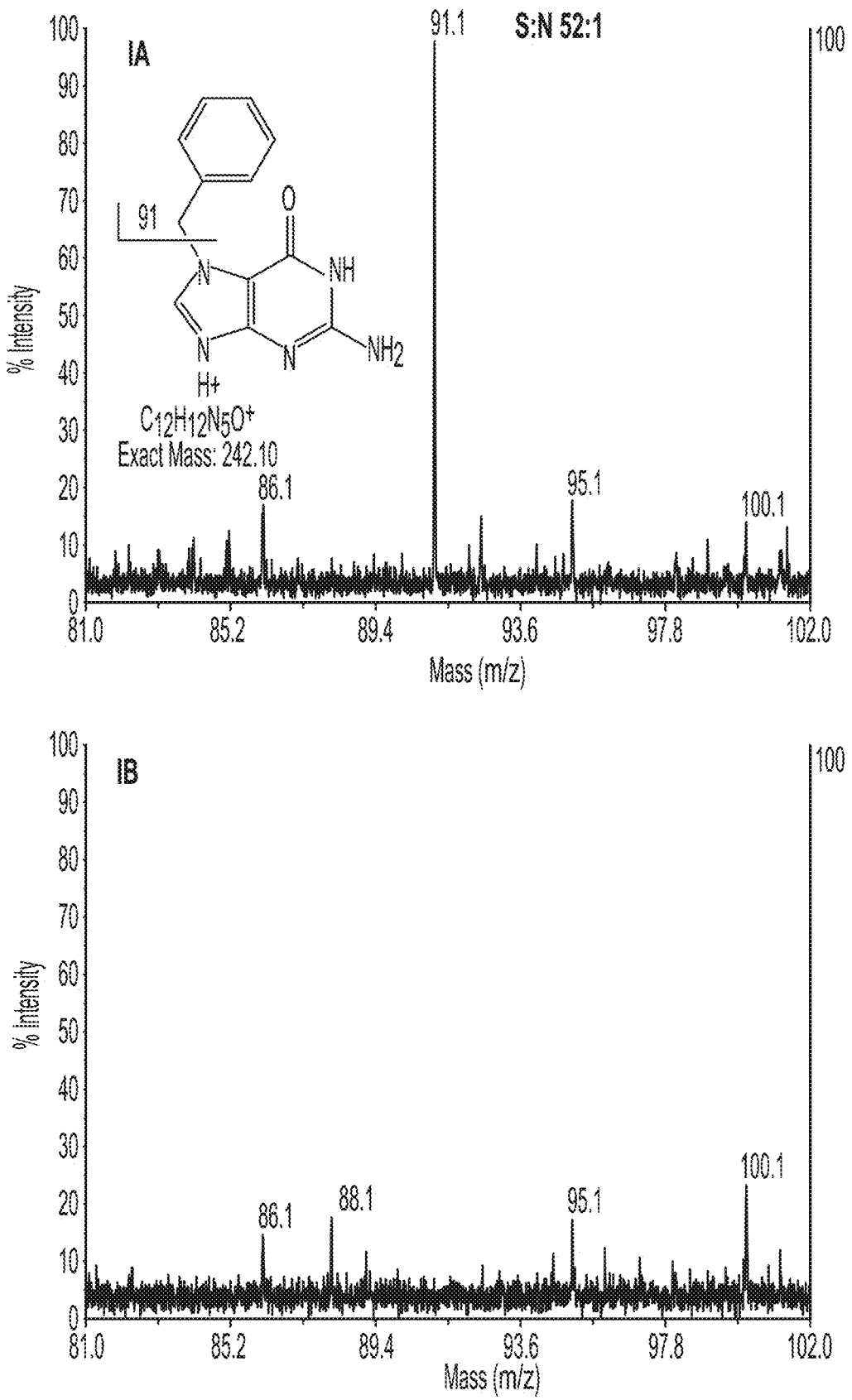
FIG. 10. Detection of N7-benzyl-dGMP. I: A, Detection of 21 amol of N7-benzyl-dGMP by JeMS2 (242→91); B, Blank (matrix). II: A, Detection of spiked benzyl-dGMP into DNA by JeMS2 (242→91); B, Blank (DNA).
Figure 10:
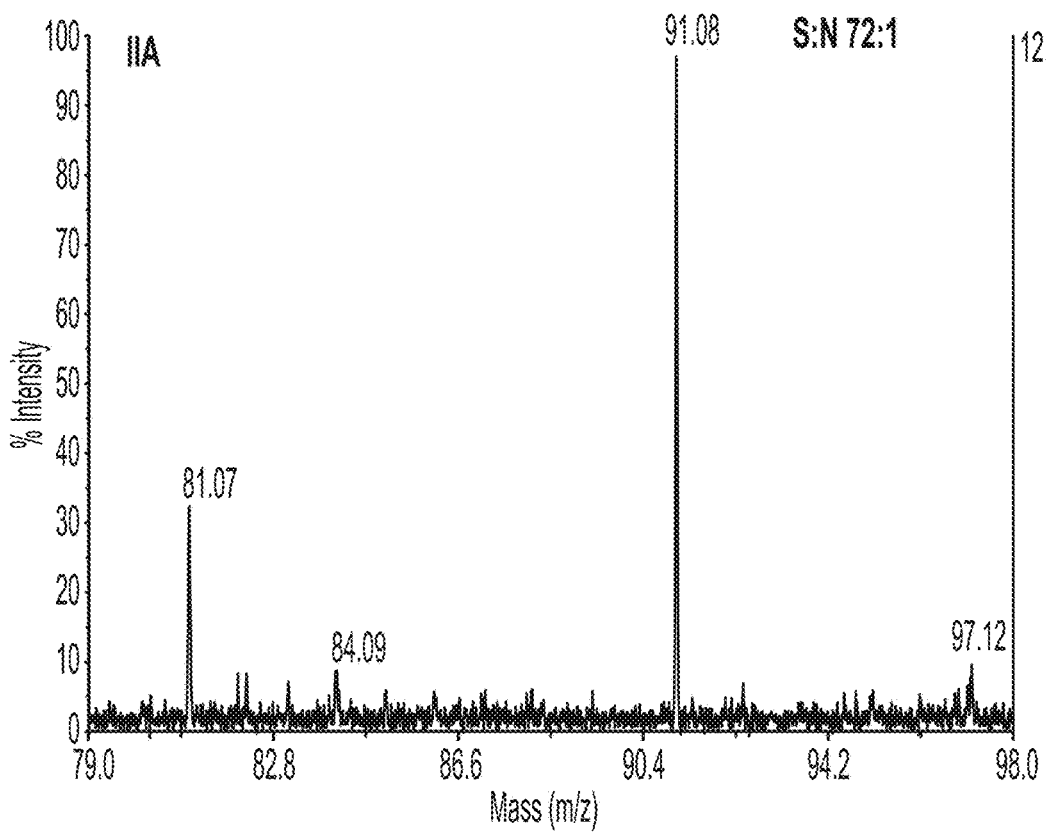
Figure 10:
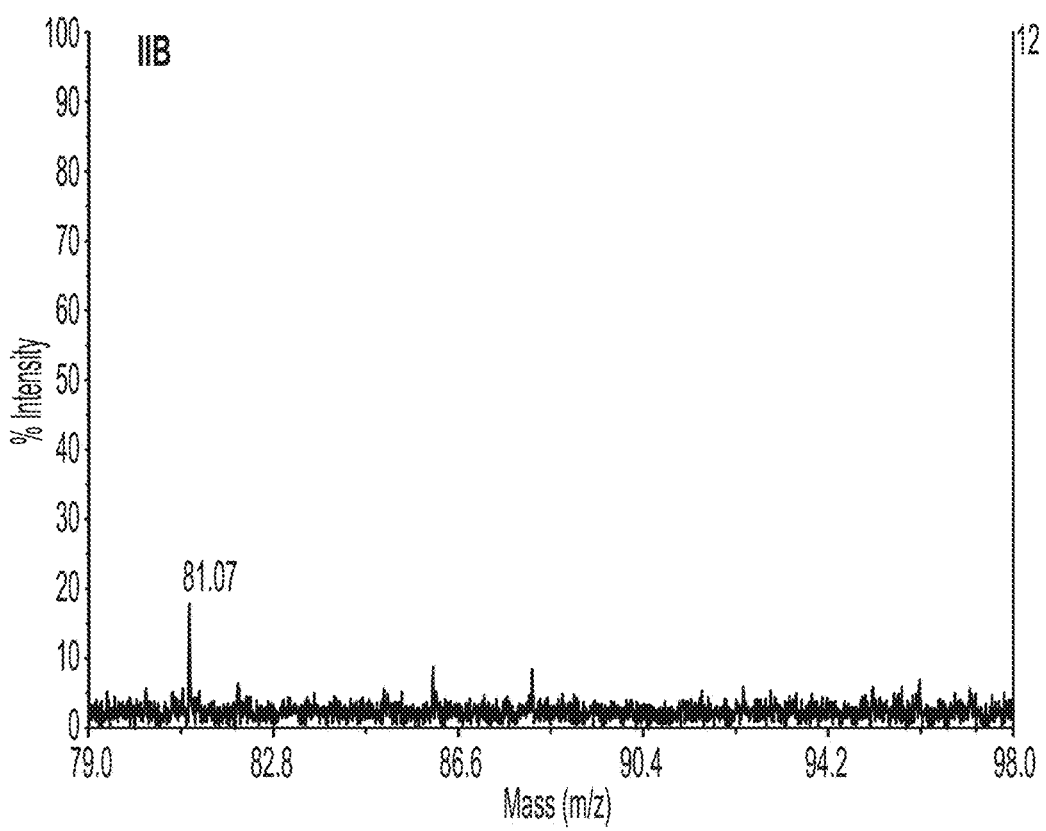

Additional data related to the JeMS2 method applied to benzyl-dGMP and DNA spiked with benzyl-dGMP are shown in FIG. 10. In FIG. 10, IA detection of 21 amol of benzyl-dGMP is observed at S/N=52. Data from a corresponding blank is shown in IB, where water was tested. We diluted the same amount of authentic benzyl dGMP into calf thymus DNA at a ratio of 6.6 benzyl dGMP in $10^8$ nucleotides and detected the benzyl cation at a S/N=72 as shown in IIA, where a blank spectrum (nonspiked calf thymus DNA) is shown in IIB.

Figure 6:
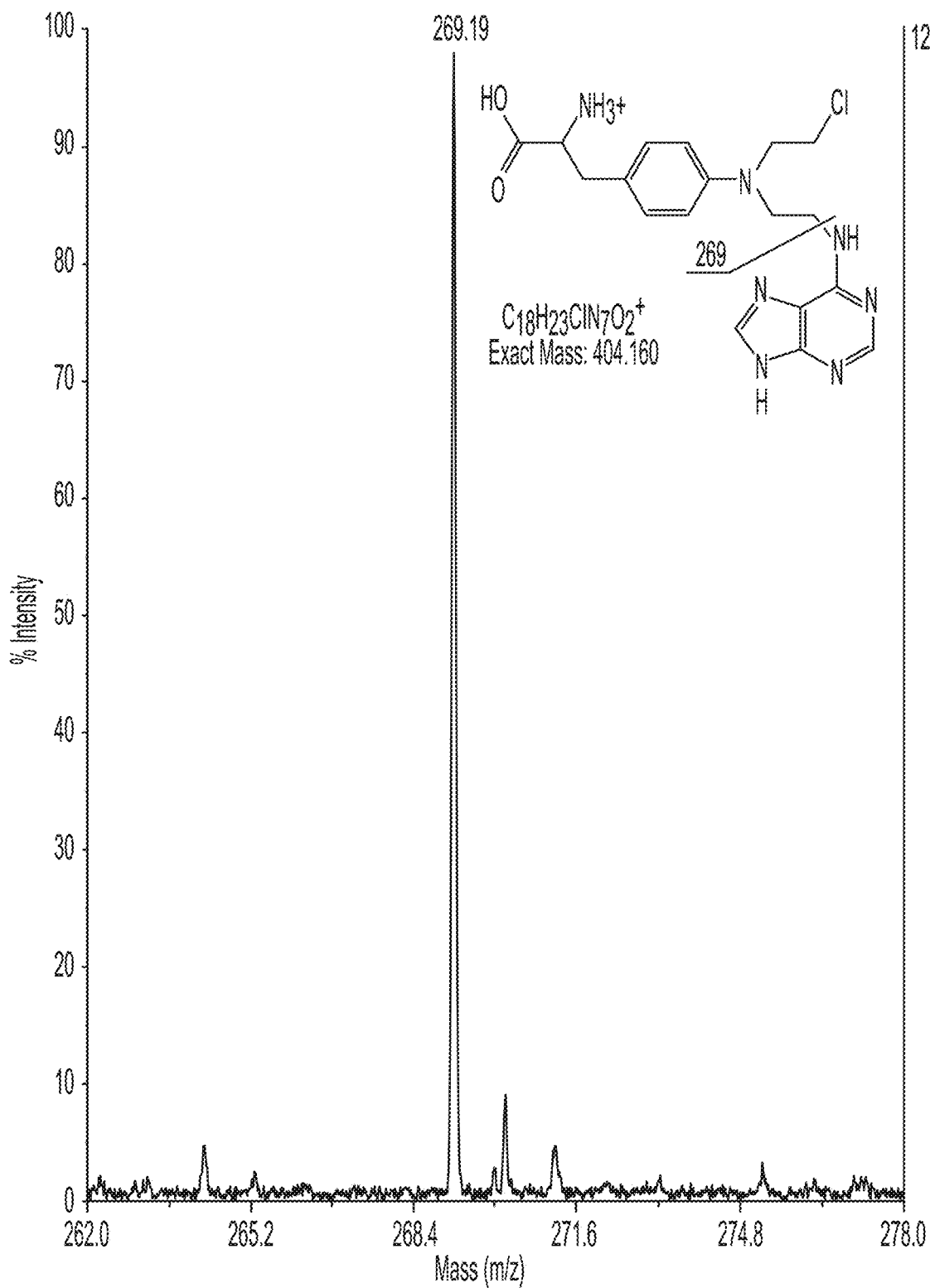
FIG. 6. JeMS2 (404→269) of a melphalan-adenine DNA adduct from the blood DNA of a chemotherapy patient undergoing treatment with melphalan.
Figure 8:
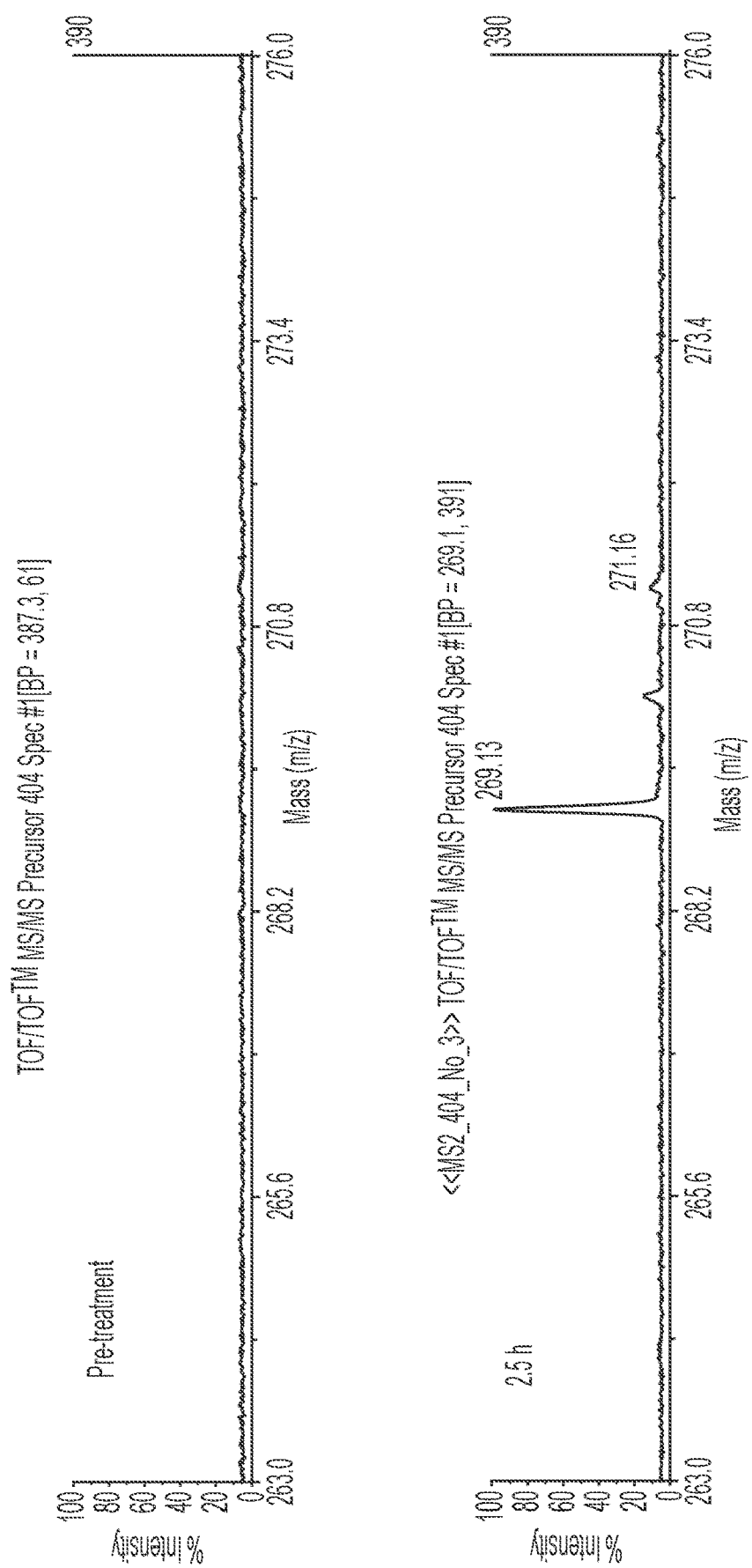
FIG. 8. Monitoring a melphalan-adenine DNA adduct in blood DNA obtained from a patient on melphalan chemotherapy for multiple melanoma at 4 different time points by JeMS2 (404→269).
Figure 8:
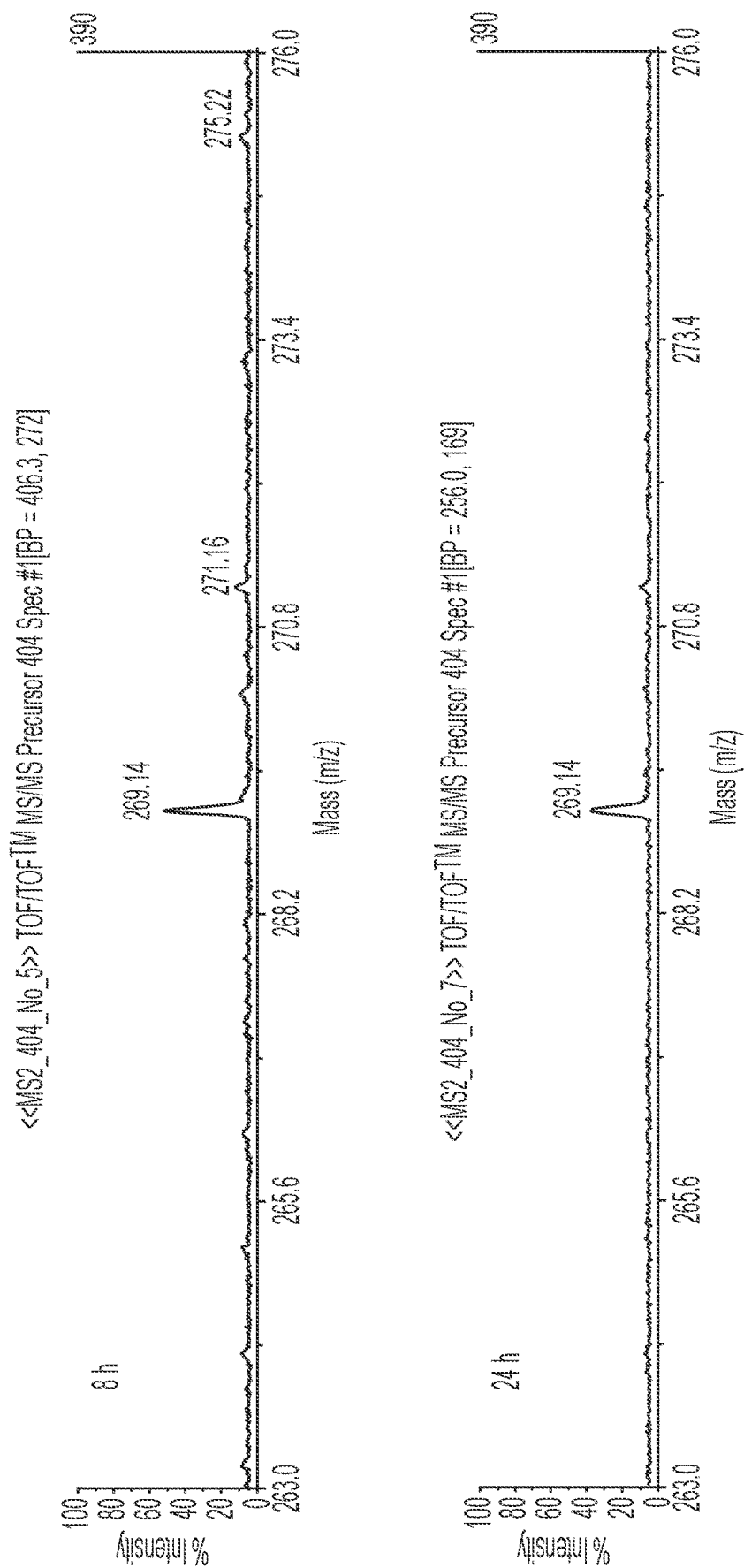

FIG. 6 shows the detection of a melphalan-adenine DNA adduct in blood buffy coat DNA obtained from a patient undergoing melphalan chemotherapy for multiple melanoma. Overall, 39 DNA samples were tested from 10 patients, providing blood at 0, 2.5, 8, and 24 h after melphalan administration (one patient lacked 8 h sample). Data for these time points for one patient are shown in FIG. 8. Interestingly, the data for the pretreatment samples (0 h) clustered at every time point relative to treatment by PCA when complete TOF/TOF data was evaluated, supporting the concept that patient DNA is more damaged by this treatment than melphalan adducts.

Figure 7:
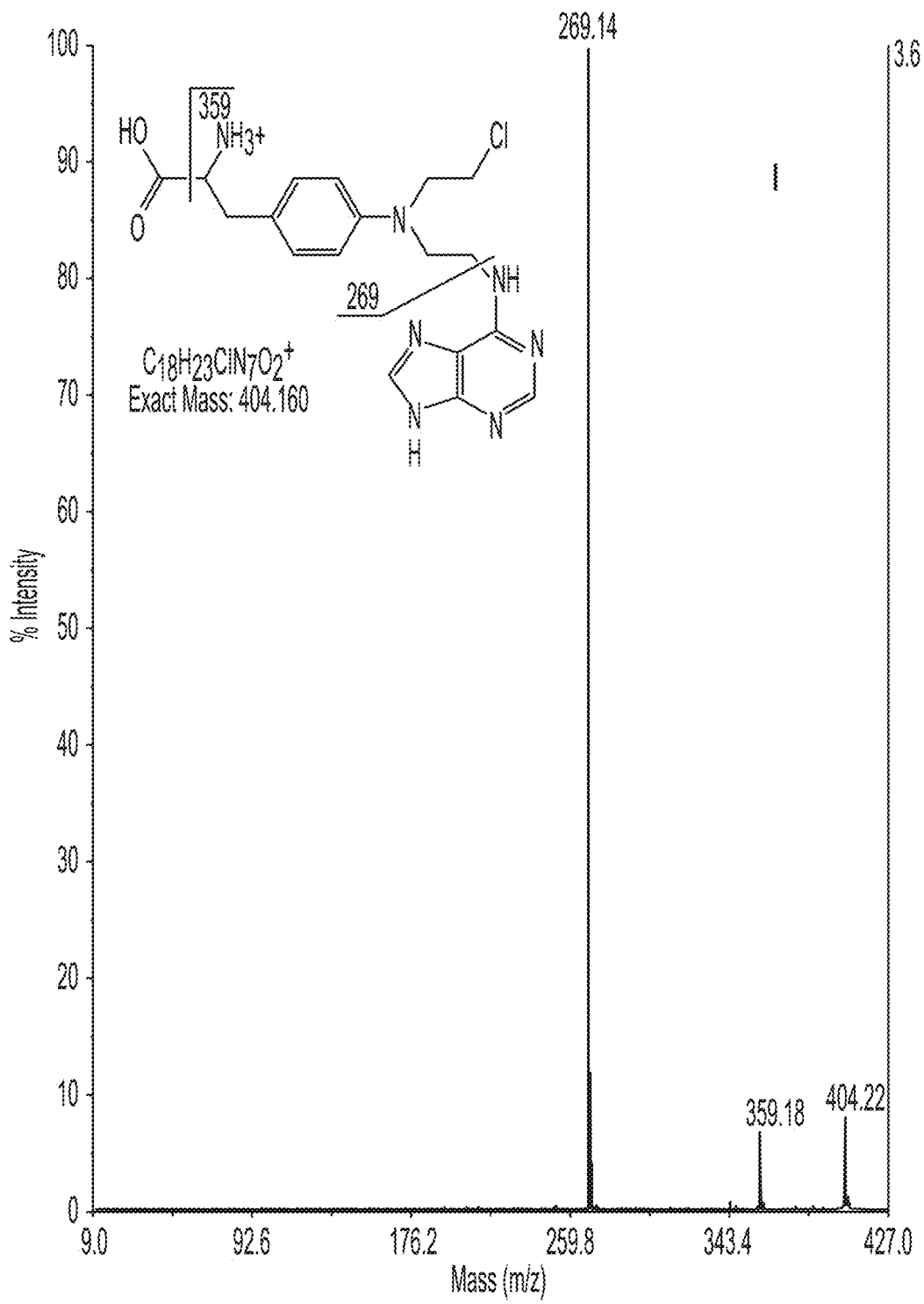
FIG. 7. JeMS2 of melphalan-modified adenine shows characteristic peaks in I: m/z 359.18 and m/z 269.14 in TOF/TOF mode from precursor ion m/z 404.22 Da; II: corresponding hydrolyzed product, m/z 341.22 and m/z 251.17 from precursor ion m/z 386.30 Da.
Figure 7:
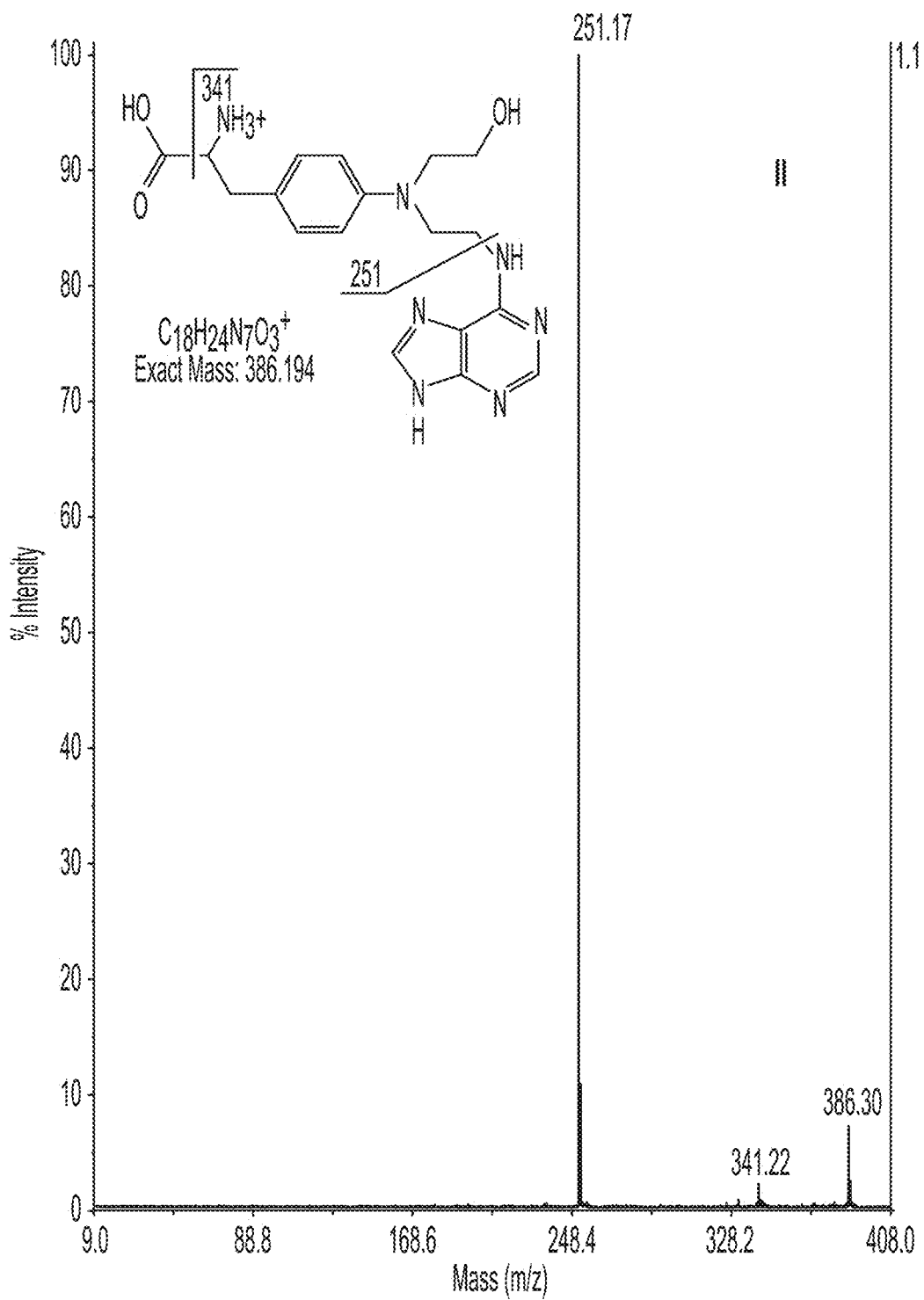

FIG. 7 shows characteristic peaks from standard adenine modified with melphalan. A, m/z 359.18 Da, and m/z 269.14 by JeMS2, where these ions arise from the precursor ion at 404.22 Da; B, similarly m/z 341.22 and m/z 251.17 are detected from the hydrolyzed product of melphalan modified A where the precursor ion is 386.30 Da.

Figure 9:
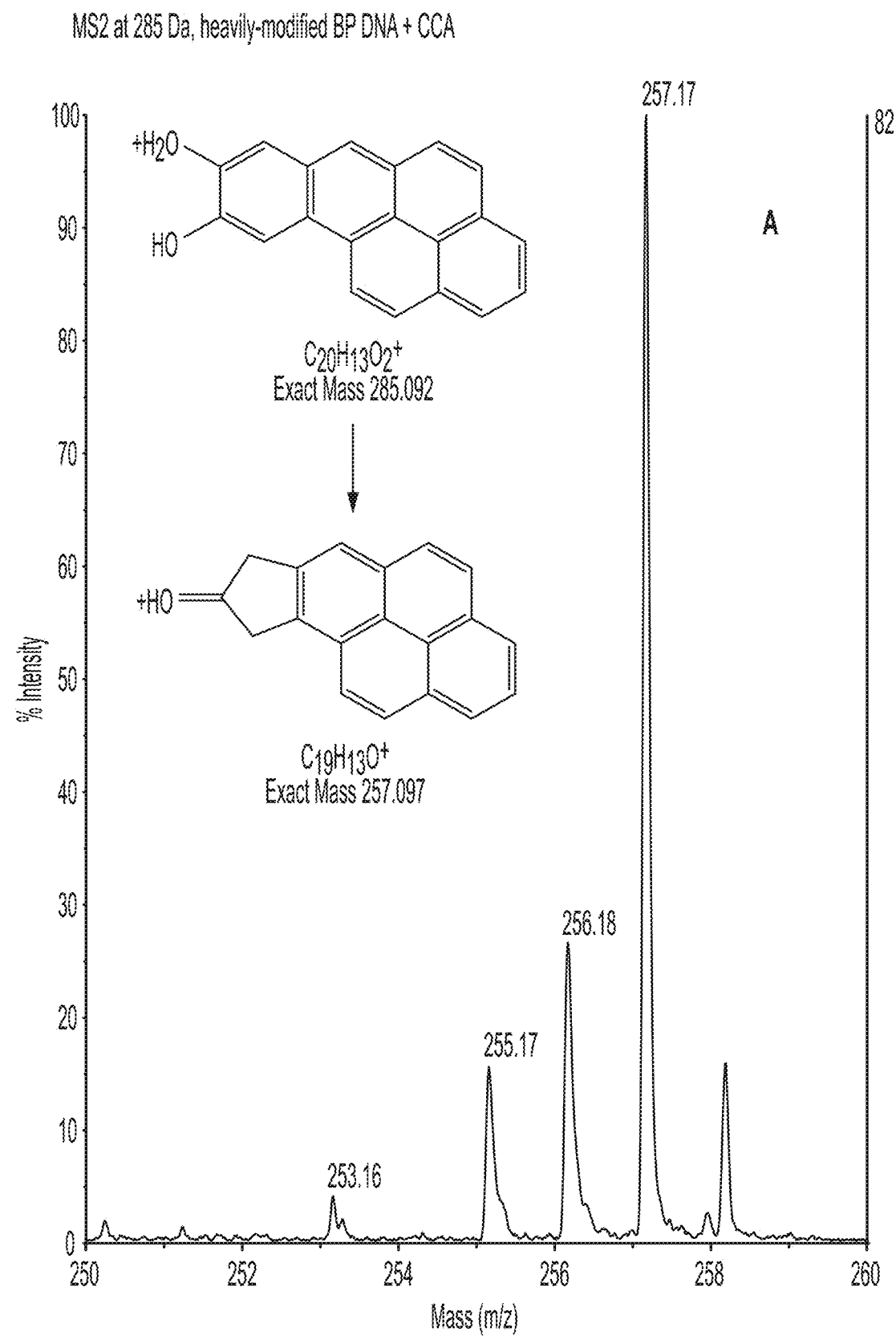
FIG. 9. Detection of a benzo[a]pyrene DNA adduct by JeMS2. A: JeMS2 (285→257) of benzo[a]pyrene diolepoxide modified calf thymus DNA. Here detection of the benzylic cation of B(a)P is seen at m/z 257.17 as a second product ion arising by loss of water from the first product ion at m/z 285.092, a pseudo MS3 process. Testing an authentic sample of DNA known to have 1 B(a)P adduct in $10^6$ nucleotides (provided by Fred Beland at NCTR; Beland, 2005), gave the analogous data shown in C (detection of m/z 257.17), relative to the spectrum from a matrix blank shown in B.
Figure 9:
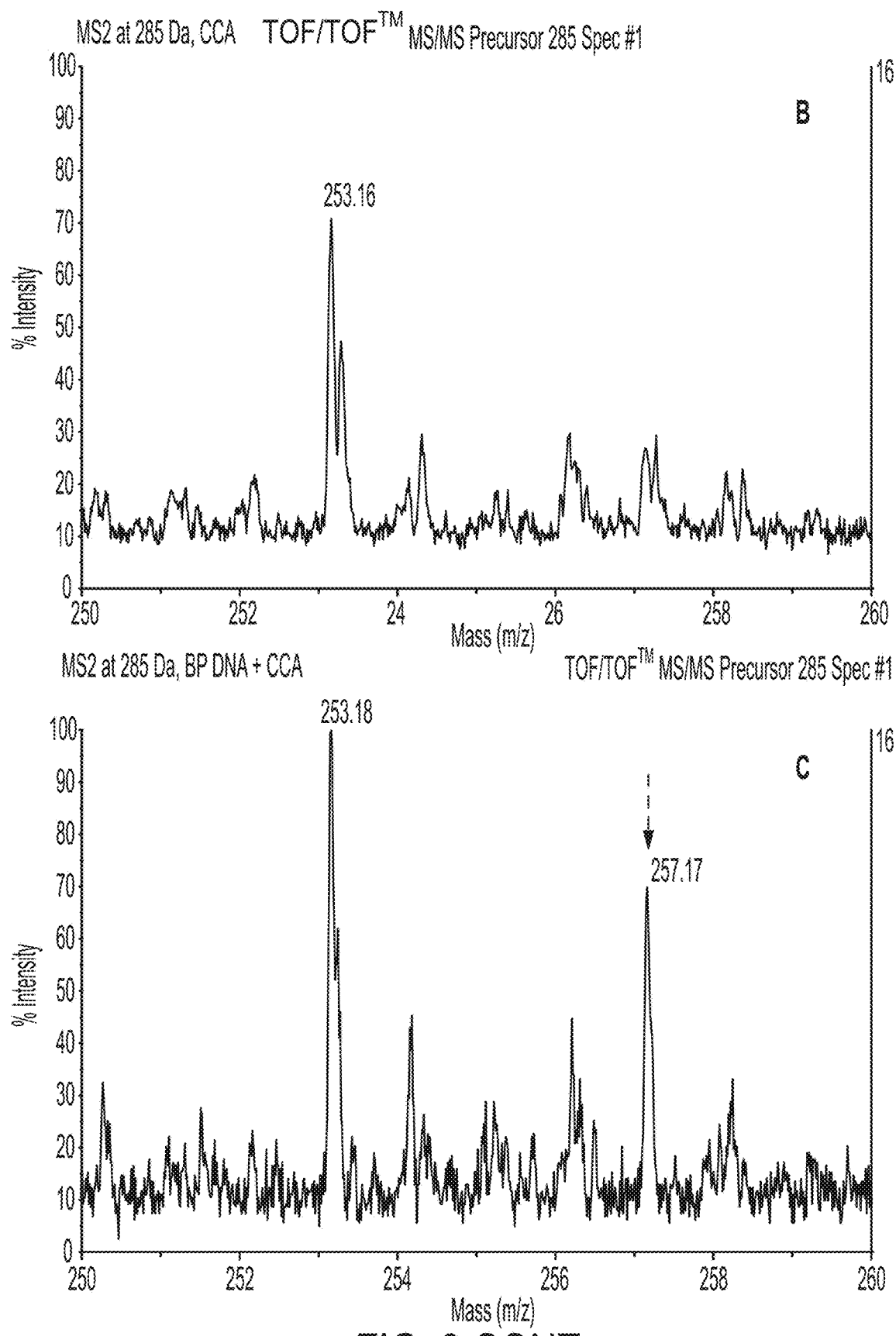

FIG. 9 shows the examination benzo[a]pyrene diolepoxide modified calf thymus DNA by JeMS2 (285→257). Here detection of the benzylic cation of B(a)P is seen at m/z 257.17 as a second product ion arising by loss of water from the first product ion at m/z 285.092, a pseudo MS3 process. Testing an authentic sample of DNA known to have 1 B(a)P adduct in $10^6$ nucleotides (provided by Fred Beland at NCTR; Beland, 2005), gave the analogous data shown in Figure C (detection of m/z 257.17), relative to the spectrum from a matrix blank shown in Figure B.

Figure 11:
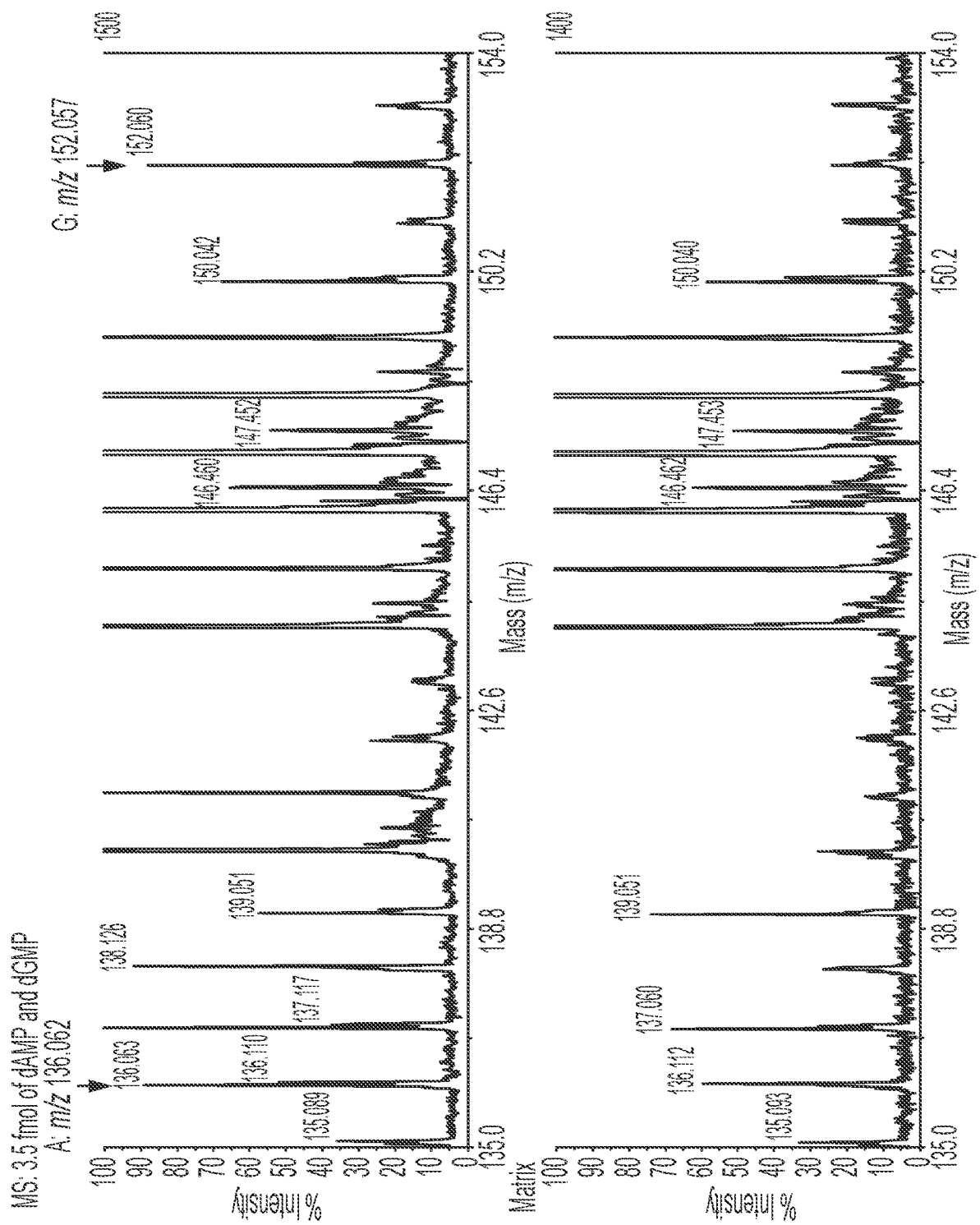
FIG. 11. JeMS of canonical nucleotides: an equimolar mixture of two nucleotides (dAMP, and dGMP, 3.5 fmol each) was subjected to JeMS giving detection of each at a S/N (signal to noise) of about 70. JeMS conditions applied to the corresponding, free nucleobases at the same level gave detection of the same (protonated nucleobases) at a S/N of about 80 (data not shown).

FIG. 11, top, demonstrates JeMS detection of canonical nucleotides: an equimolar mixture of two nucleotides (dAMP, and dGMP, 3.5 fmol each) was subjected to JeMS giving signals for corresponding protonated nucleobases with an observed S/N of about 70. Bottom, matrix alone.

Figure 12:
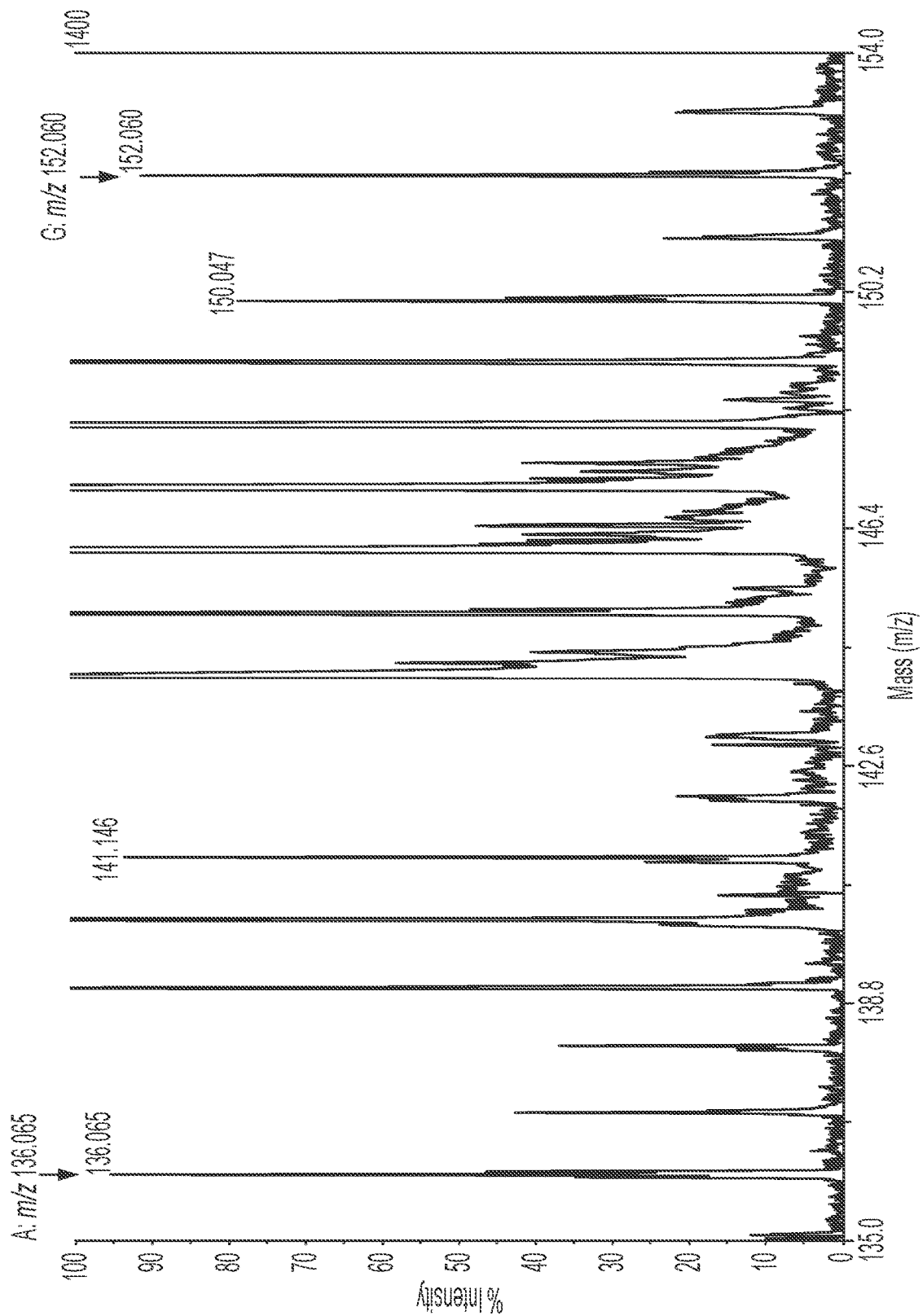
FIG. 12. Detection by JeMS of the A (m/z 136.065) and G (m/z 152.060) nucleobases of the RNA oligomer, ATGATGATG. Amount of oligomer applied to the target: 3.4 pg (providing 3.7 fmol each of A, T and G). S/N=100 for the A and G peaks.

FIG. 12 shows detection by JeMS of the A (m/z 136.065) and G (m/z 152.060) nucleobases of the RNA oligomer, ATGATGATG. Amount of oligomer applied to the target: 3.4 pg (providing 3.7 fmol each of A, T and G). S/N=100 for the A and G peaks.

Figure 13:
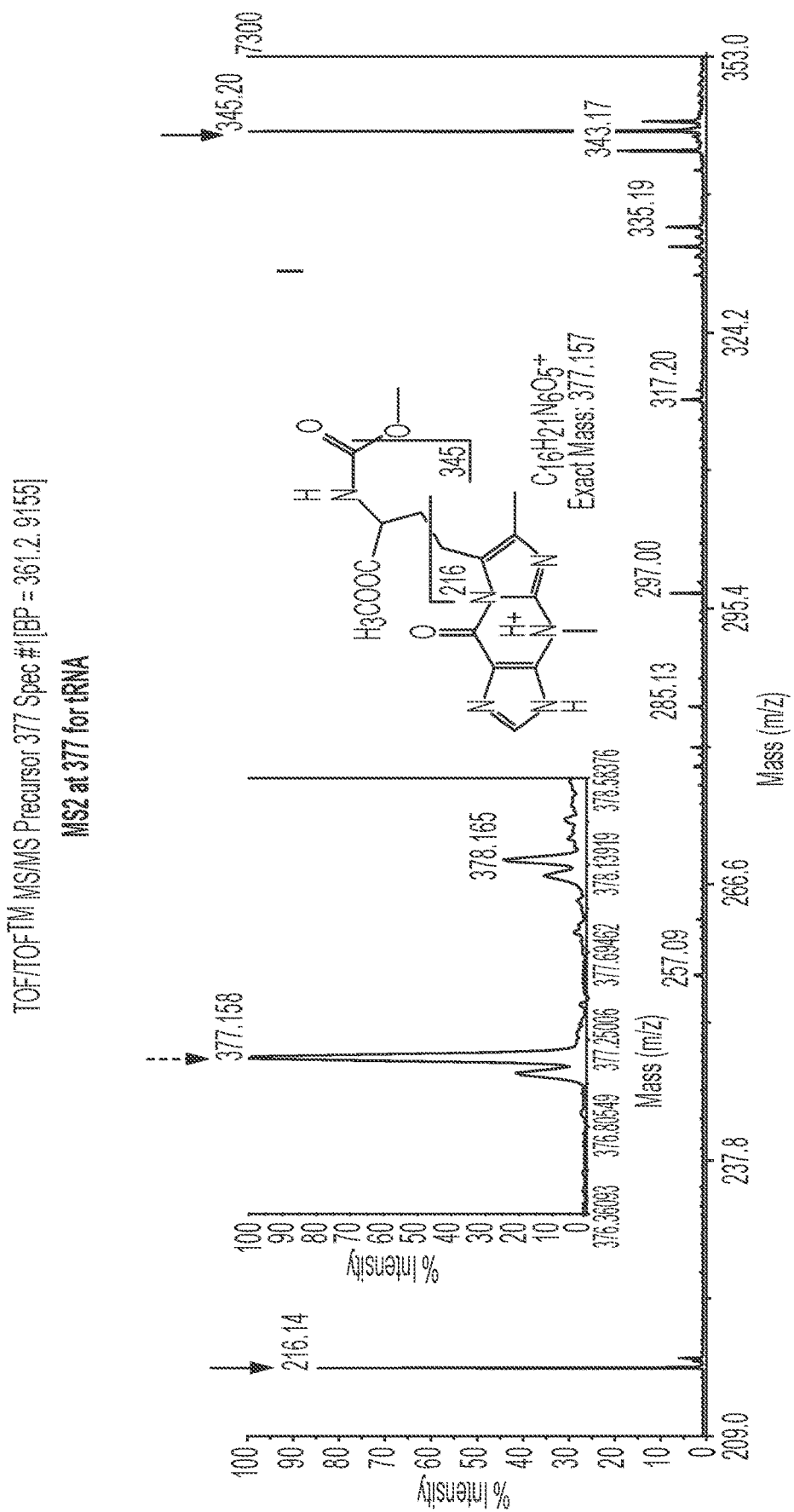
FIG. 13. I. Detection of wybutosine of tRNA by JeMS2 (377→345). II. JeMS2 of CCA matrix alone. Inset: detection of wybutosine of tRNA by JeMS.
Figure 13:
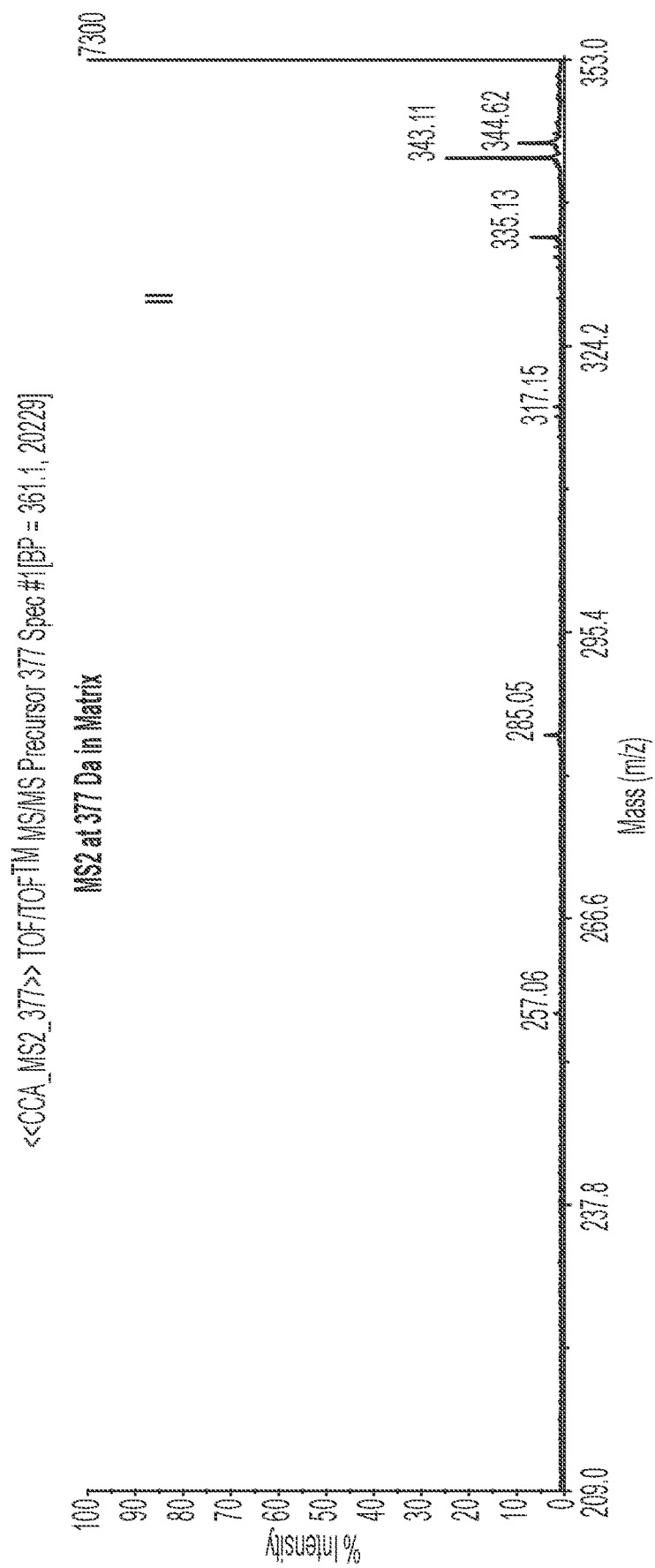

FIG. 13 shows detection of wybutosine of tRNA by JeMS2 (377→345) (I) and CCA matrix alone (II) (Inset: detection by JeMS of wybutosine of tRNA)

Figure 14:
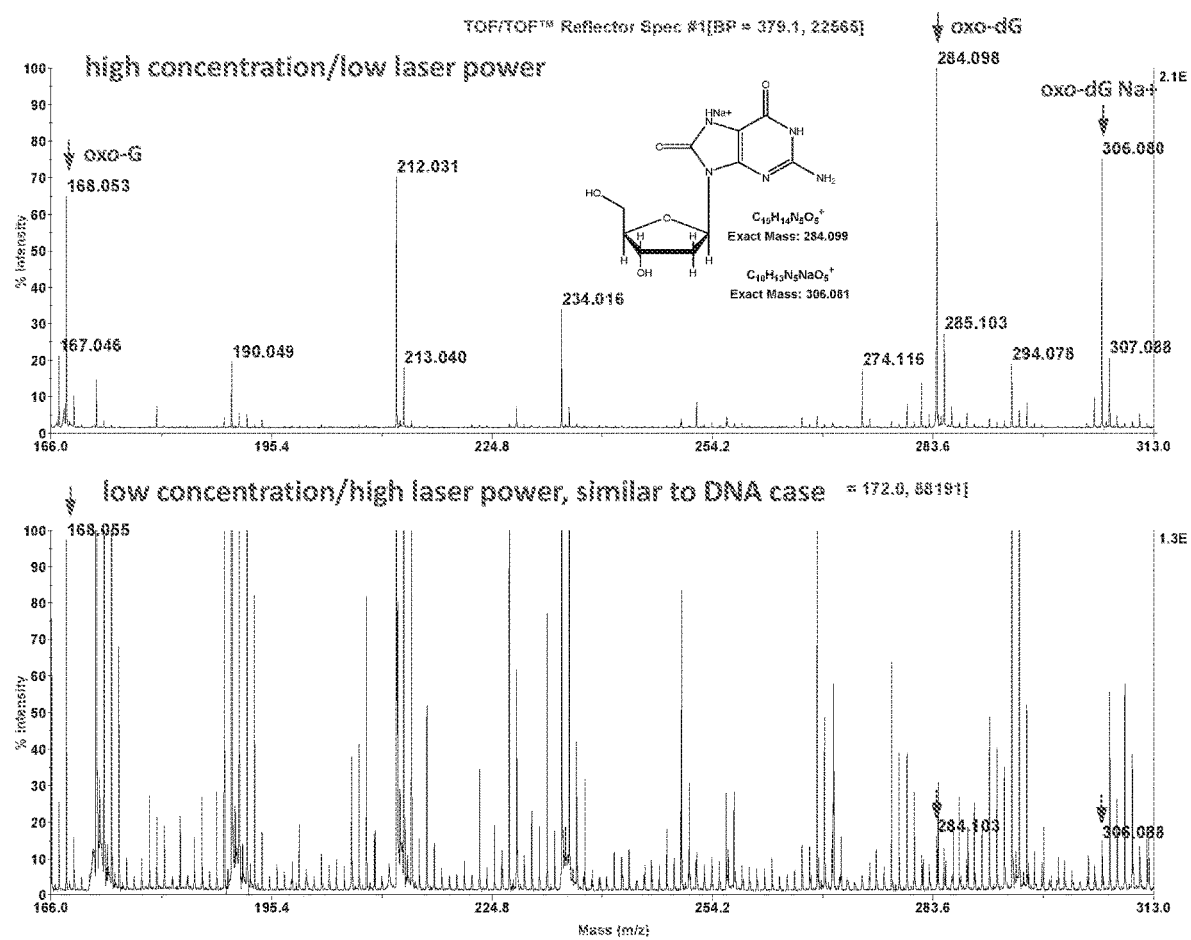
FIG. 14. JeMS of a nucleoside, 8-oxo-dG: higher laser power on the bottom (close to the matrix storm level) enhances sensitivity. Top: 900 fmol per spot of analyte; Bottom: 9 fmol per spot of analyte.

FIG. 14 demonstrates application of JeMS to the analysis of a nucleoside, 8-oxo-dG: higher laser power on the bottom (close to the matrix storm level) enhances sensitivity. Top: 900 fmol per spot of analyte; Bottom: 9 fmol per spot of analyte.

Figure 15:
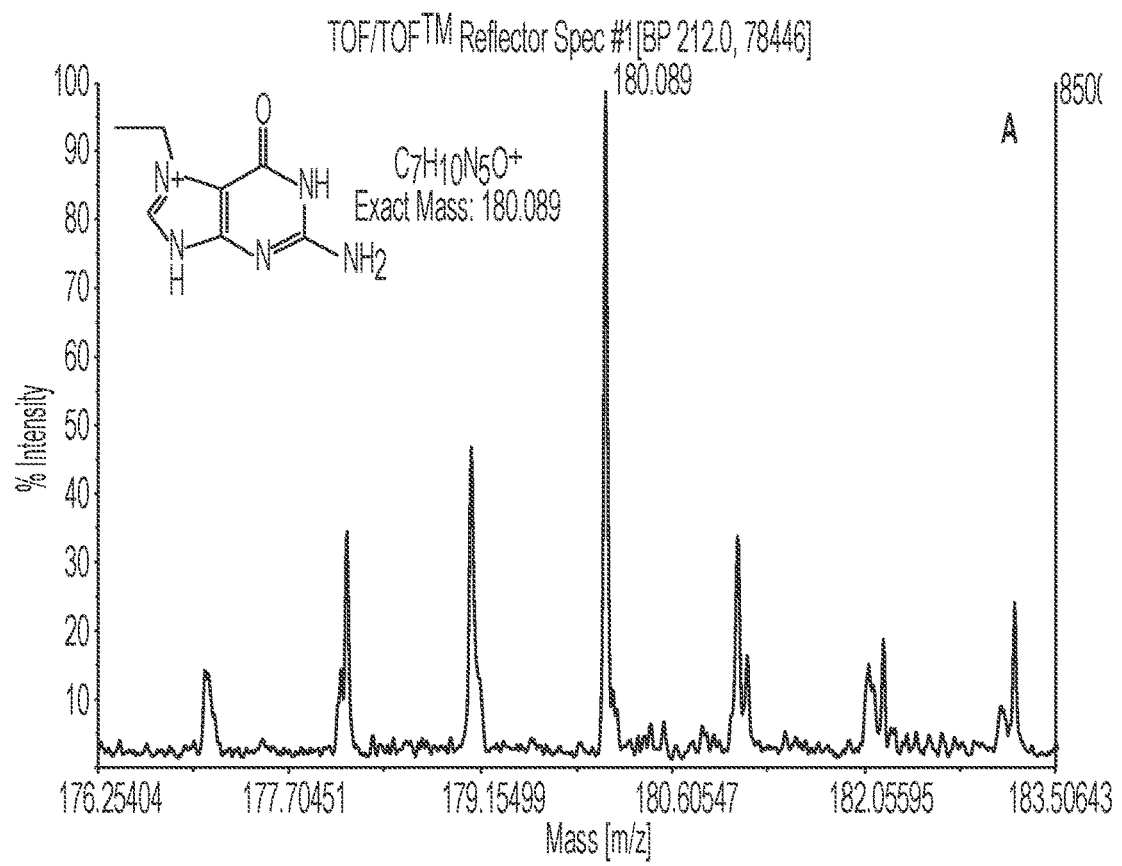
FIG. 15. JeMS of four samples of nucleic acid species: A: ethyl-G obtained by reaction of CT DNA with by methanesulfonic acid ethyl ester; B: hydroxyethyl-G by reaction with Lomustine; C: Bz-C, Bz-A and Bz-G by reaction with benzyl bromide; D: SO-A and SO-G by reaction with styrene oxide (SO: styrene oxide).
Figure 15:
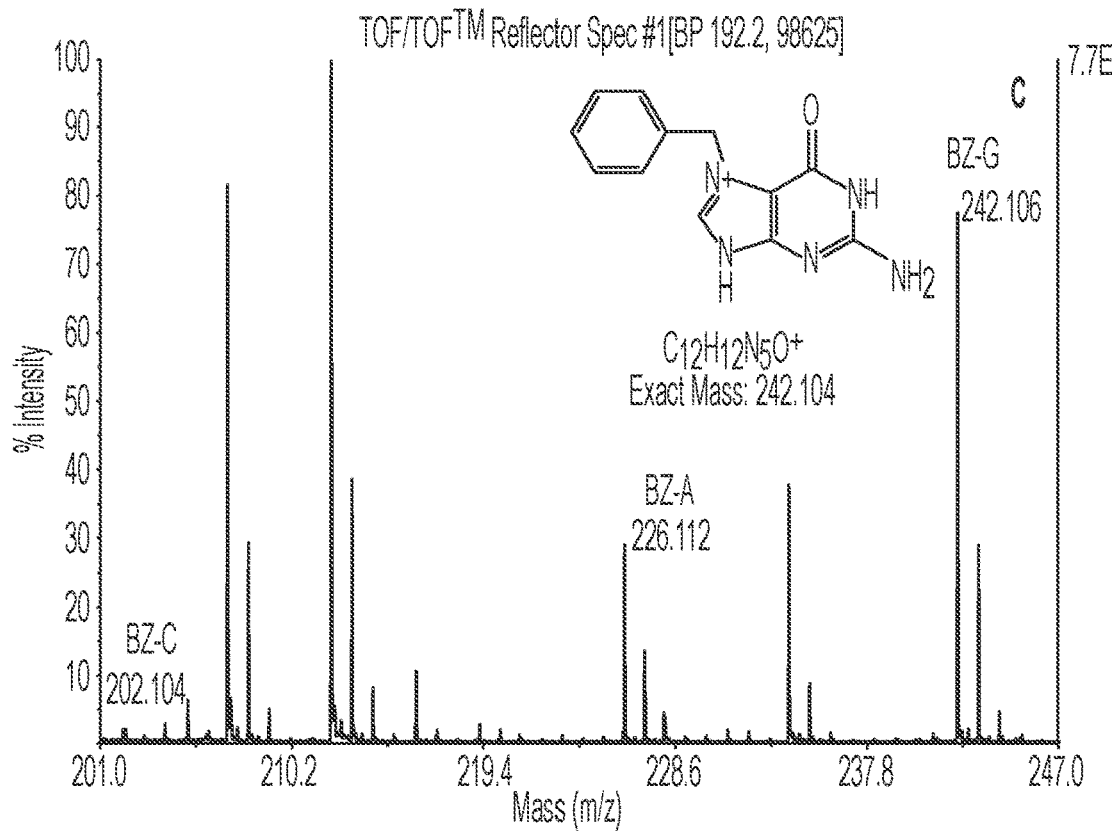
Figure 15:
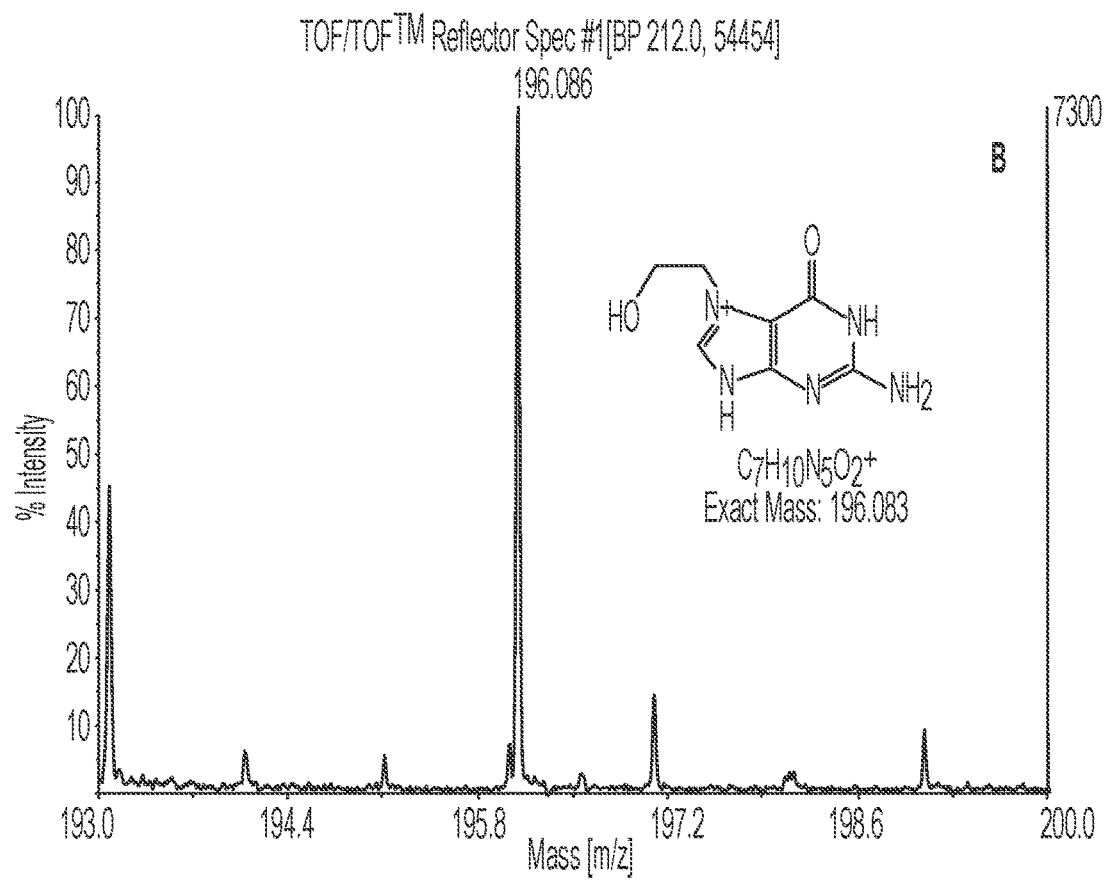
Figure 15:
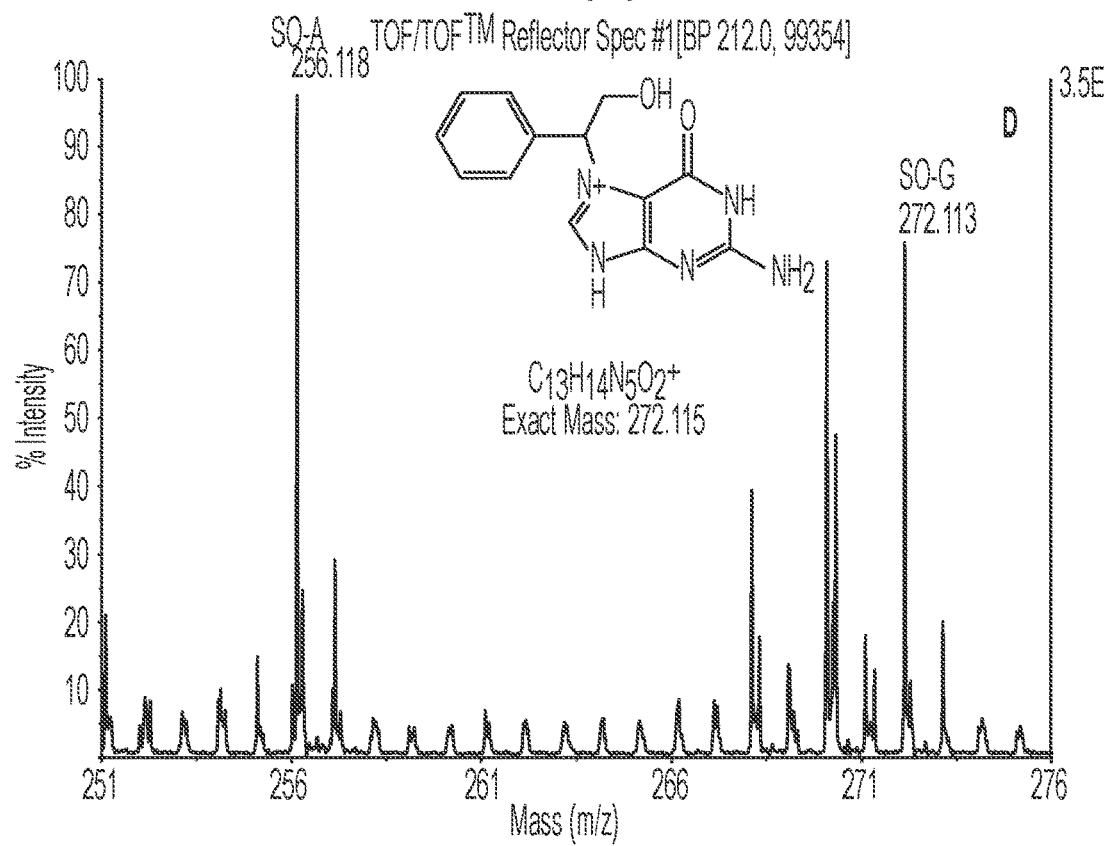

FIG. 15 shows JeMS of four samples of modified DNA. A, Detection of ethyl-G in DNA modified with methanesulfonic acid ethyl ester; B, hydroxyethyl-G in DNA modified by Lomustine; C, Bz-C, Bz-A and Bz-G in DNA modified by benzyl bromide; D, SO-A and SO-G in DNA modified by styrene oxide (SO: styrene oxide).

Data not shown: JeMS testing of type X tRNA from Sigma Aldrich detected 12 of the distinctive 42 isobaric natural modifications known for this substance.

REFERENCES CITED

Balbo, S., Turesky, R. J., Villalta, P. W. (2014) DNA Adductomics, Chem. Res. Toxicol. 27, 356-366.

Basanta-Sanchez, M., Temple, S., Ansari, S. A., D'Amico. A., Agris P. F. (2015) Attomole quantification and global profile of RNA modifications: Epitranscriptome of human neural stem cells, Nucleic Acid Res, 18, 1-10.

Cantara, W. A., Crain, P. F., Rozenski, J., McCloskey, J. A., Harris, K. A., Zhang, X., Vendeix, F. A. P., Fabris, D., Agris, P. F. (2010) The RNA modification database, RNAMDB: 2011 update, Nucleic Acids Res. 39, 195-201.

Douthwaite, S., Kirpekar, F. (2007) Identifying modifications in RNA by MALDI mass spectrometry, Methods Enzymol, 425, 3-20.

Ezzati, M. (2017) Worldwide trends in body-mass index, underweight, overweight, and obesity from 1975 to 2016: a pooled analysis of 2416 population-based measurement studies in 128.9 million children, adolescents, and adults, Lancet 390, 2627-2642.

Fitzgerald, m. C., Parr, G. R., Smith. L. M. (1993) Basic Matrices for the Matrix-Assisted Laser Desorption Ionization Mass Spectrometry of Proteins and Oligonucleotides, Anal. Chem. 65, 3204-3211.

Gao, X., Tan, B. H., Sugrue, R. J., Tang, K. (2013) MALDI mass spectrometry for nucleic acid analysis, Top Curr. Chem. 331, 55-77.

Gatson, K. W., Limbach, P. A. (2014) The identification and characterization of non-coding and coding RNAs and their modified nucleosides by mass spectrometry, RNA Biol. 11, 1568-1585.

Geacintov, N. E., Broyde, S. (2010) The Chemical Biology of DNA Damage, Wiley-VCH, Weinheinm, ISBN: 978-3-527-32295-4

Giessing, A. M. B., Kirpekar, F. (2012) Mass spectrometry in the biology of RNA and its modifications, J. Proteomics 75, 3434-3449.

He, C. (2010) RNA epigenetics? Nature American Inc. 482.

Hemeryck, L. Y., Decloedt, A. I., Vanden Bussche, J., Geboes, K. P., Vanhaecke, L (2015) High resolution mass spectrometry based profiling of diet-related deoxyribonucleic acid adducts, Anal. Chimica Acta, 892, 123-131.

Hendry, L. B., Mahesh, V. B., Bransome Jr. E. D., Ewing, D. E. (2007) Small molecule intercalation with double stranded DNA: Implications for normal gene regulation and for predicting the biological efficacy and genotoxicity of drugs and other chemicals, Mutation Res. 623, 53-71.

Hossain, M., Limbach, p. L. (2007) Mass spectrometry-based detection of transfer RNAs by their signature endonuclease digestion products, RNA 13, 295-303.

Honisch, C. (2016) The World of Nucleic Acid-Based Mass Spectrometry for Microbial and Viral Detection, in MALDI-TOF Mass Spectrometry in Microbiology, 141-156.

Hursting, S. D., O'Flanagan, C. H., Bowers, L. W. (2015) Breaking the Obesity-Cancer Link, The SCIENTIST, 29, 27-33.

Li, S., Mason, C. (2014) The Pivotal Regulatory Landscape of RNA Modifications, Annu. Rev. Genom. Hum. Genet. 15, 127-150.

Monien, B. H., Schumacher, F., Herrmann, K., Glatt, H., Turesky, R. J., Chesne, C. (2014) Simultaneous Detection of Multiple DNA Adducts in Human Lung Samples by Isotope-Dilution UPLC-MS/MS, Anal. Chem. 87, 641-648.

Moschel, R. C., Hudgins, W. R., Dipple, A. (1979) Selectivity in Nucleoside Alkylation and Aralkylation in Relation to Chemical Carcinogenesis, J. Org. Chem., Vol. 44, No. 19.

Nordhoff, E., Kirpekar, F., Karas, M., Cramer, R., Hahner, S., Hillenkamp, F., Kristiansen, K., Roepstorff, P., Lezius, A. (1994) Comparison of IR- and UV-matrix-assisted laser desorption/ionization mass spectrometry of oligodeoxynucleotides, Nucl. Acids Res. 22, 2460-2465.

Nordhoff. E., Kirpekar, F., Roespstorff, P. (1996) Mass Spectrometry of Nucleic Acids, Mass Spectrum. Rev. 15, 67-138.

Paulines, M. J., Limbach, P. A., (2017) Stable Isotope Labeling for Improved Comparative Analysis of RNA Digests by Mass Spectrometry, 25, 551-561. J. Am. Soc. Mass Spectrom.

Peterson, D. S. (2007) Matrix-free methods for laser desorption/ionization mass spectrometry, Mass Spectrom. Rev. 26, 19-34.

Pinak, M. (2003) Electrostatic energy analysis of 8-oxoguanine DNA lesion-molecular dynamics study, Comput. Biol. Chem. 27, 431-441.

Poirier, M. C. (2016) Linking DNA Adduct Formation and Human Cancer Risk in Chemical Carcinogenesis, Environ. Mol. Mutagen 57, 499-507.

Pottenger, L. H., Andrews. L. S., Bachman, A. N., Boogaard, P. J., Cadet, J., Embry, M. R., Farmer, P. B., Himmelstein, M. W., Jarabek, A. M., Martin, E. A., Mauthe, R. J., Persaud, R., Preston, R. J., Schoeny, R., Skare, J., Swenberg, J. A., Williams, G. M., Zeiger, E., Zhang, F., Kim, J. H. (2014) An organizational approach for the assessment of DNA adduct data in risk assessment: case studies for aflatoxin B1, tamoxifen and vinyl chloride, Crit. Rev. Toxicol. 44, 348-391.

Rainer, M., Qureshi, M. N., Bonn, G. K. (2011) Matrix-free and material-enhanced laser desorption/ionization mass spectrometry for the analysis of low molecular weight compounds, Anal Bioanal. Chem. 400, 2281-2288.

Ritter, S. K., Meet the Sentinels, C&EN Nov. 20, 2017, p. 26.

Satterlee, J. S., Basanta-Sanchez, M., Blanco, S., Li, J. B., Meyer, K., Pollock, J., Sadri-Vakili, G., Rybak-Wolf, A. (2014) Novel RNA Modifications in the Nervous System: Form and Function, J. Neurosci. 34, 15170-15177.

Sattsangi, P. D., Leonard, N. J., Frihart, C. R. (1977) 1,N2-Ethenoguanine and N2,3-Ethenoguanine. Synthesis and Comparison of the Electronic Spectral Properties of These Linear and Angular Triheterocycles Related to the Y Bases, J. Org. Chem., Vol. 42, No. 20, 3292-3296.

Schrader, W., Linscheid, M. (1997) Styrene oxide DNA adducts: in vitro reaction and sensitive detection of modified oligonucleotides using capillary zone electrophoresis interfaced to electrospray mass spectrometry, Arch. Toxicol. 71: 588-595.

Stemmler E. A., Buchanan M. V., Hurst G. B., Hettich R. L. (1994) Structural characterization of polycyclic aromatic hydrocarbon dihydrodiol epoxide DNA adducts using matrix-assisted laser desorption/ionization Fourier transform mass spectrometry, Anal. Chem. 66(8):1274-85.

Stemmler E. A., Buchanan M. V., Hurst G. B., Hettich R. L. (1995) Analysis of modified oligonucleotides by matrix-assisted laser desorption/ionization Fourier transform mass spectrometry, Anal. Chem. 67(17):2924-30.

Stornetta, A., Zimmermann, M., Cimino, G. D., Henderson, P. T. (2016) DNA Adducts from Anticancer Drugs as Candidate Predictive Markers for Precision Medicine, Chem Res. Toxicol, 30, 388-409.

Stover, E. H., Konstantinopoulos, P. A., Matulonis, U. A., Swisher, E. M. (2016) Biomarkers of Response and Resistance to DNA Repair Targeted Therapies, Clin, Cancers. Res. 5661-5660.

Su, D., Chan, C. T. Y., Gu, C., Lim, K. S., Chionh, Y. H., McBee, M. E., Russell, B. S., Babu, R., Begley, T. J. Dedon, P. C. (2014) Quantitative analysis of tRNA modifications by HPLC-coupled mass spectrometry, Nature Protocols, (4):828-841.

Taghizadeh, K., McFaline, J. L., Pang, B., Sullivan, M., Dong, M., Plummer, E., Dedon, P. C. (2008) Quantification of DNA damage products resulting from deamination, oxidation and reaction with products of lipid peroxidation by liquid chromatography isotope dilution tandem mass spectrometry, Nature Protocols 3, 1287-1298.

van den Boom, D. and Berkenkamp, S. (2007) MALDI-MS of Nucleic Acids and Practical Implementations in Genomics and Genetics, in MALDI MS: A Practical Guide to Instrumentation, Methods and Applications (eds F. Hillenkamp and J. Peter-Katalinić), Wiley-VCH Verlag GmbH & Co. KGaA, Weinheim, Germany.

Villalata, P. W., Balbo, S. (2017) The Future of DNA Adductomic Analysis, Int. J. Mol. Sci, 8, 1870-1890.

Walker, B. N., Stolee, J. A., Vertes, A. (2012) Nanophotonic Ionization for Ultratrace and Single-Cell Analysis by Mass Spectrometry, Anal. Chem. 84, 7756-7762.

Wohlrab, F., (1992) Enzyme Probes in Vitro, Methods Enzymol 3212, 294-301.

Wang, P., Giese, R. W. (2017) Recommendations for quantitative analysis of small molecules by matrix-assisted laser desorption ionization mass spectrometry, J. Chromatogr. A, 1486, 35-41.

Wu, K. J., Steding, A., Becker, C. H. (1993) Matrix-assisted laser desorption time-of-flight mass spectrometry of oligonucleotides using 3-hydroxypicolinic acid as an ultraviolet-sensitive matrix, Rapid Commun. Mass Spectrom, 7, 142-146; PMID: 8457722.

Wu, D., Liu, B., Yin, J., Xu, T., Zhao, S., Xu, Q., Chen, X. (2017) Detection of 8-hydroxydeoxyguanosine (8-OHdG) as a biomarker of oxidative damage in peripheral leukocyte DNA by UHPLC-MS/MS, J. Chromatogr. 1064, 1-6.

Yu, B., Chen, X. (2010) Analysis of miRNA Modifications, Methods Mol. Biol. 592, 137-148.

Zenobi, R. and Knochenmuss, R. (1998) Ion Formation in MALDI Mass Spectrometry, Mass Spectrometry Review, 17:337-366

Zhu, Y. F., Chung, C. N., Taraneko, N. I., Allman, S. L., Martin, S. A., Haff, L., Chen, C. H. (1996) The study of 2,3,4-trihydroxyacetophenone and 2,4,6-trihydroxyacetophenone as matrices for DNA detection in matrix-assisted laser desorption/ionization time-of-flight mass spectrometry, Rapid Commun. Mass Spectrom, 10, 383-388.

INCORPORATION BY REFERENCE

All of the U.S. patents and U.S. and PCT patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are encompassed by the following claims.

What is claimed is:

1. A mass spectrometry method for detecting a modified nucleobase in a nucleic acid species, comprising
    a) providing a sample, wherein the sample comprises:
        (i) a modified nucleobase attached in N-glycosidic linkage to a ribose or deoxyribose moiety of a nucleic acid, nucleoside, nucleotide or oligonucleotide; and
        (ii) a matrix, wherein the matrix comprises at least one Brønsted acidic proton source; and
    b) subjecting the sample to at least one laser pulse, wherein the laser fluence is about 70% to about 95% of the matrix storm level.

2. The method of claim 1, wherein the laser is a UV laser or an IR laser.

3. The method of claim 1, wherein the laser fluence is about 80% to about 95% of the matrix storm level.

4. The method of claim 1, wherein at least two synchronized laser pulses are used that differ in wavelength.

5. The method of claim 1, wherein the matrix comprises glycerol, urea, or succinic acid.

6. The method of claim 1, wherein the matrix comprises a compound having a carboxylic acid moiety.

7. The method of claim 6, wherein the compound is α-cyano-4-hydroxycinnamic acid or 4-chloro-α-cyanocinnamic acid.

8. The method of claim 1, wherein Brønsted acidic proton source is selected from the group consisting of phosphoric acid, ammonium chloride, formic acid, acetic acid, trifluoroacetic acid, and heptafluorobutyric acid.

9. The method of claim 1, wherein the molar ratio of the overall nucleobases in the sample to the matrix is about 0.03 to about 0.3.

10. The method of claim 1, wherein the laser fluence is about 90% to about 95% of the matrix storm level.

11. A mass spectrometry method for detecting a canonical nucleobase in a nucleic acid species, comprising
    a) providing a sample, wherein the sample comprises:
        (i) a canonical nucleobase attached in N-glycosidic linkage to a ribose or deoxyribose moiety of a nucleic acid, nucleoside, nucleotide or oligonucleotide;
        (ii) a matrix, wherein the matrix comprises at least one Brønsted acidic proton source; and
        (iii) the molar ratio of the overall nucleobases in the sample to the matrix is about 0.03 to about 0.3; and
    b) subjecting the sample to at least one laser pulse, wherein the laser fluence is about 70% to about 95% of the matrix storm level.

12. The method of claim 11, wherein the nucleic acid is DNA or RNA.

13. The method of claim 11, wherein the laser is a UV laser or an IR laser.

14. The method of claim 11, wherein the laser fluence is about 80% to about 95% of the matrix storm level.

15. The method of claim 11, wherein at least two synchronized laser pulses are used that differ in wavelength.

16. The method of claim 11, wherein the matrix comprises glycerol, urea, or succinic acid.

17. The method of claim 11, wherein the matrix comprises a compound having a carboxylic acid moiety.

18. The method of claim 17, wherein the compound is α-cyano-4-hydroxycinnamic acid or 4-chloro-α-cyanocinnamic acid.

19. The method of claim 11, wherein the Bøonsted acidic proton source is selected from the group consisting of phosphoric acid, ammonium chloride, formic acid, acetic acid, trifluoroacetic acid, and heptafluorobutyric acid.

20. The method of claim 11, wherein the molar ratio of the overall nucleobases in the sample to the matrix is about 0.1.

* * * * *